United States Patent
Littrup et al.

(10) Patent No.: US 7,499,745 B2
(45) Date of Patent: Mar. 3, 2009

(54) MULTIDIMENSIONAL BIOELECTRICAL TISSUE ANALYZER

(75) Inventors: Peter Littrup, Bloomfield Hills, MI (US); Robert Duncan, Tejeras, NM (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 1743 days.

(21) Appl. No.: 09/794,612

(22) Filed: Feb. 27, 2001

(65) Prior Publication Data

US 2001/0051774 A1 Dec. 13, 2001

Related U.S. Application Data

(60) Provisional application No. 60/185,413, filed on Feb. 28, 2000.

(51) Int. Cl.
*A61B 5/05* (2006.01)
(52) U.S. Cl. .................................................. 600/547
(58) Field of Classification Search ................ 600/547
See application file for complete search history.

(56) References Cited

U.S. PATENT DOCUMENTS

| | | | | |
|---|---|---|---|---|
| 4,407,300 A | 10/1983 | Davis | | 128/734 |
| 4,870,578 A | 9/1989 | Vysin et al. | | 364/413.05 |
| 4,920,490 A | 4/1990 | Isaacson | | 364/413.13 |
| 4,955,383 A | 9/1990 | Faupel | | 128/653 R |
| 5,099,844 A | 3/1992 | Faupel | | 128/653.1 |
| 5,143,079 A | 9/1992 | Frei et al. | | 128/734 |
| 5,187,096 A | 2/1993 | Giaever et al. | | 435/291 |
| 5,217,014 A | 6/1993 | Hahn et al. | | 128/640 |
| 5,260,871 A * | 11/1993 | Goldberg | | 600/320 |
| 5,320,101 A | 6/1994 | Faupel et al. | | 128/653.1 |
| 5,351,697 A | 10/1994 | Cheney et al. | | 128/734 |
| 5,381,333 A | 1/1995 | Isaacson et al. | | 364/413.13 |
| 5,390,110 A | 2/1995 | Cheney et al. | | 364/413.13 |
| 5,415,164 A | 5/1995 | Faupel | | 128/630 |
| 5,427,098 A | 6/1995 | Faupel et al. | | 128/653.1 |
| 5,465,730 A | 11/1995 | Zadenkoochak et al. | | 128/734 |
| 5,544,662 A * | 8/1996 | Saulnier et al. | | 600/547 |
| 5,560,357 A | 10/1996 | Faupel et al. | | 128/635 |
| 5,588,429 A | 12/1996 | Isaacson et al. | | 128/734 |
| 5,626,146 A | 5/1997 | Barber et al. | | 128/734 |

(Continued)

OTHER PUBLICATIONS

Vauhkonen PJ, Vauhkonen M, Savolainen T, Kaipio JP. Three-dimensional electrical impedance tomography based on the complete electrode model. IEEE Trans Biomed Eng. Sep. 1999;46(9):1150-60.*

*Primary Examiner*—Max Hindenburg
*Assistant Examiner*—Jeffrey G Hoekstra
(74) *Attorney, Agent, or Firm*—Townsend and Townsend and Crew LLP

(57) ABSTRACT

A method and apparatus that use complex impedance measurements of tissue in human or animal bodies for the detection and characterization of medical pathologies is disclosed. An analysis of the complex impedance measurements is performed by a trained evaluation system that uses a nonlinear continuum model to analyze the resistive, capacitive, and inductive measurements collected from a plurality of sensing electrodes. The analysis of the impedance measurements results in the construction of a multidimensional space that defines the tissue characteristics, which the trained evaluation system uses to detect and characterize pathologies. The method and apparatus are sufficiently general to be applied to various types of human and animal tissues for the analysis of various types of medical pathologies.

169 Claims, 13 Drawing Sheets

U.S. PATENT DOCUMENTS

| | | | |
|---|---|---|---|
| 5,639,444 A | 6/1997 | Klaveness | 424/9.321 |
| 5,660,177 A | 8/1997 | Faupel et al. | 128/639 |
| 5,678,547 A | 10/1997 | Faupel et al. | 128/653.1 |
| 5,697,369 A | 12/1997 | Long, Jr. et al. | 128/65.31 |
| 5,715,821 A | 2/1998 | Faupel | 128/653.1 |
| 5,746,214 A | 5/1998 | Brown et al. | 128/693 |
| 5,807,251 A | 9/1998 | Wang et al. | 600/407 |
| 5,810,742 A * | 9/1998 | Pearlman | 600/547 |
| 5,823,957 A | 10/1998 | Faupel et al. | 600/397 |
| 5,919,142 A | 7/1999 | Boone et al. | 600/547 |
| 6,201,990 B1 | 3/2001 | Wexler et al. | 600/547 |

* cited by examiner

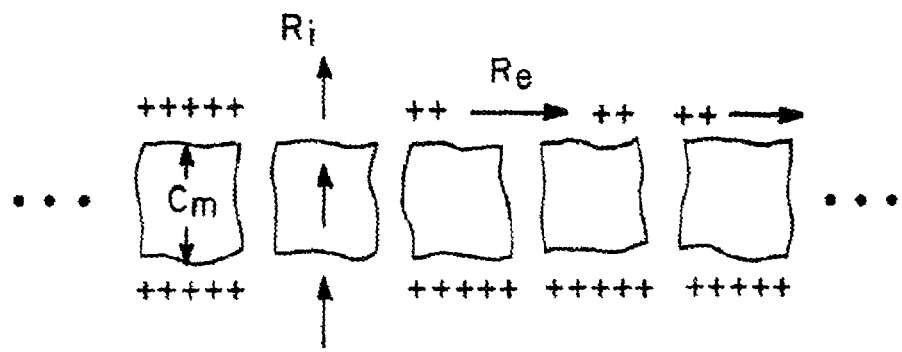
FIG. 2(a)
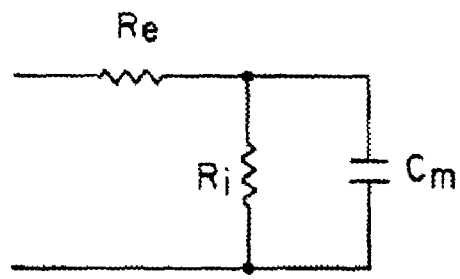
FIG. 2(b)
Prior Art
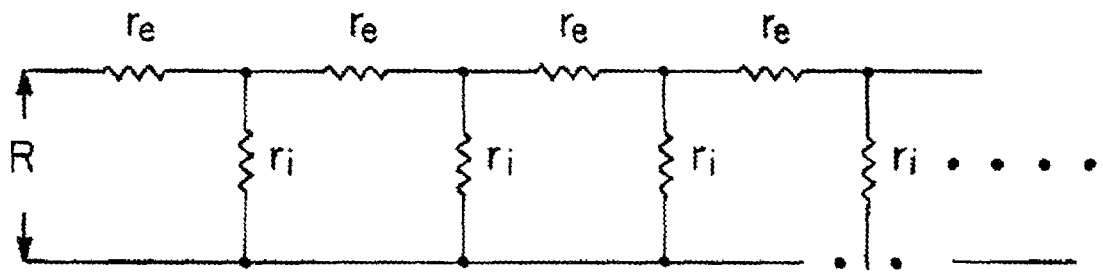
FIG. 2(c)(i)
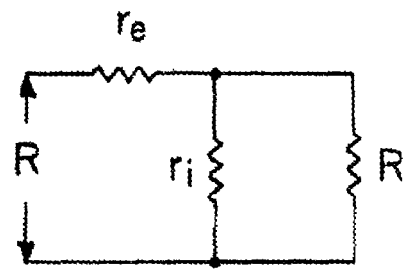
FIG. 2(c)(ii)

MULTIDIMENSIONAL BIOELECTRICAL TISSUE ANALYZER

This application is a nonprovisional of and claims the benefit of U.S. Appl. No. 60/185,413, filed on Feb. 28, 2000, the disclosure of which is herein incorporated by reference in its entirety for all purposes.

1. FIELD OF THE INVENTION

This invention relates to the diagnosis of medical pathologies in tissues and internal organs of a human or animal body. More particularly, the invention relates to the diagnosis of oncologic pathologies in tissues or internal organs of a human or animal body and to the diagnosis of other pathologies in the cardiac, pulmonary, neurologic, and skeletal systems using bioelectrical impedance measurements.

2. BACKGROUND OF THE INVENTION

2.1. Introduction

There is an ongoing need in medicine for methods and apparatuses that can accurately detect and characterize medical pathologies within tissues and internal organs in a human or animal body. There is currently a particular need for a versatile method and apparatus to provide safe, reliable, and low-cost analysis of such pathologies, which may occur in a wide variety of systems. Examples of such medical pathologies include cancerous tumors and lesions, bone fractures, and diseased tissue in the cardiopulmonary or neurological systems. Presently, the identification of such medical pathologies is accomplished primarily through the use of imaging techniques such as x-ray technology, mammography, and various cross-sectional techniques, which include computed tomography (CT), magnetic resonance imaging (MRI), ultrasound (US), nuclear medicine [i.e., single-photon emission computed tomography (SPECT)], and positron-emission tomography (PET).

Each of these existing technologies has drawbacks, however. For example, x-rays, mammography, and CT scans all use ionizing radiation and therefore present certain health risks to a patient, such as cell mutations. Also, both CT scans and MRI involve procedures that are relatively expensive, thereby hampering their widespread use. MRI in particular requires the expertise of highly trained personnel for extended periods of time to operate the devices and to interpret the results. Mammography is particularly uncomfortable for the patient since it requires that the breast being studied be compressed to allow more uniform tissue density, better x-ray penetration, and tissue stabilization. More importantly, these methods rely principally on two-dimensional images; three-dimensional data are compressed in one direction, thereby disguising three-dimensional structure information that can be critical for accurate diagnosis. Additionally, with the exception of SPECT and PET, imaging of tissue generally involves only an anatomic and gross morphologic assessment of general architecture and composition. The cost and availability of functional imaging techniques such as SPECT and PET has yet to be sufficiently reliably documented to justify their application in routine procedures. The lack of functional, or tissue characterization, imaging makes standard imaging non-specific. Lack of specificity causes further testing and increases costs.

As a result of these drawbacks, the medical community continues to explore alternative imaging and diagnostic techniques that can improve safety and reliability, and reduce cost. One area that has received limited attention involves the measurement of the electromagnetic field of living organisms; methods and devices that use such measurements are relatively crude and exploit only a portion of the data that can be collected. The invention described in this application is directed to a sophisticated method and apparatus that uses any information available from bioelectrical impedance measurements for the diagnosis of medical pathologies.

2.2. Basis of Cell Membrane Electrical Potential

An understanding of the electrical characteristics of organic tissue begins at the cellular level. Cell membranes are semipermeable lipid-protein bilayers that behave as leaky electrical capacitors. A typical cell membrane is approximately 7 nm thick and has ions distributed asymmetrically across it. The ionic gradients resulting from this asymmetric distribution are maintained in living cells by ionic pumps. Because ions naturally tend to diffuse from a higher concentration to a lower one, the concentration gradient across the cell membrane results in an electrical potential $V_m$. In a typical cell, this electrical potential is about −70 mV so that the strength of the cell's electrical field is substantial, of the order of 1 MV/m. This large electrical field affects the transport of charged particles through the cell membrane, and any physiological change that affects the ionic transport and permeability characteristics of the cell membrane can thus alter this electrical field in a measurable way.

The predominant intracellular cation is $K^+$. If a cell membrane is permeable to $K^+$ but not to $Cl^-$, then positive $K^+$ ions will diffuse down its concentration gradient across the cell membrane, resulting in an overall positive electric charge on the outside of the cell membrane and a negative charge inside the cell. This will continue until the Nernst potential difference of about 61 mV is reached, the Nernst potential defining an equilibrium point at which further diffusion of $K^+$ out of the cell is opposed by the presence of the internal negative electrical charge. In contrast, the predominant extracellular cation is $Na^+$, which will tend to flow down its concentration gradient into the cell. The $Na^+/K^+$ ATPase pump maintains the chemical gradient by pumping $Na^+$ out of the cell and pumping $K^+$ into the cell, against their respective gradients. Without these gradients, and the pumps to maintain them, there would be no cell membrane electrical potential. There may also be a direct contribution of other electrogenic pumps to the cell membrane potential, such as the $Ca^{2+}$ or the $H^{3O}$ pumps, which function in a similar manner.

One change in the electromagnetic character of the cell results from depolarization of the cell membrane, wherein the strength of the electropotential $V_m$ is reduced. This may occur in at least four different ways: (1) a change in the concentration of the permanent ions in the cell's cytoplasm or extracellular space; (2) a change in the permeability of the cell membrane; (3) a change in the transport of the electrogenic pumps; and (4) a redistribution of heavy ions, which may be a response for Norden-Strom's radiographic observations. All of these changes have been observed in proliferating cells, mitogenesis, and malignant transformation, making this depolarization a viable characteristic signature that can be used in diagnosis. Studies have confirmed that proliferating cells are relatively depolarized when compared to their non-dividing or resting counterparts. See, for example, H. G. Sachs, P. H. Stambrook, and J. D. Ebert, *Changes in membrane potential during the cell cycle*, Exp. Cell Res., 83, 362 (1974), which is herein incorporated by reference. Ionic fluxes, intracellular ionic composition, and transport mechanisms associated with mitogenesis thus all change during proliferation.

2.3. Transepithelial Electrical Potential and Cancer

Epithelial cells line many solid organs if secretion and absorption are part of their function. Examples of such organs include the breast, stomach, intestines, colon, prostate, kidney, uterus, nasopharynx, esophagus, and lung, all of which absorb and secrete various ions and water. These organs are also the sites of common malignancies, and several studies have demonstrated that transepithelial depolarization is an early feature of premalignant states. See, for example, I. Zs-Nagy, G. Lustyik, V. Zs-Nagy, B. Zarandi, and C. Bertoni-Freddari, *Intracellular Na+:K+ratios in human cancer cells as revealed by energy dispersive X-ray microanalysis*, J. Cell Biol., 90, 769 (1981), which is herein incorporated by reference. The human breast provides a specific example: epithelial cells line the terminal ductal lobular units (TDLU) of the breast, absorbing and secreting various ions and water. The transepithelial electrical potential is negative when comparing the luminal side (apical membrane) relative to the more hyperpolarized abluminal, or bloodstream, side (basolateral membrane). The apical cell membrane is permeable to $Na^-$, thereby allowing $Na^+$ to enter the cell down its electrical and concentration gradient. The $Na^+/K^+$ ATPase pump then extrudes $Na^+$ into the abluminal space across the basolateral membrane and water either flows through the cell or through tight junctions between cells.

The transepithelial electrical potential $V_T$ is thus derived from the difference of the apical $V_A$ and the basolateral $V_{BL}$ potentials of cells arranged in an epithelial sheet: $V_T=V_{BL}-V_A$. This is shown pictorially in FIG. 2, where three epithelial cells are depicted. In the figure, the abluminal breast parenchyma is at the bottom, and the epithelial cells sit on the basement membrane, denoted BM. The cell membrane is divided into distinct apical and basolateral domains by the tight junctions. Gap junctions and their associated connexin proteins provide more intercellular transport communication within the membrane. The potential at the basolateral side of the cell sheet is at $V_{BL}=-100$ mV while the apical cell membrane is at a potential of $V_A=-70$ mV. This results in a net transepithelial voltage of $V_T=-30$ mV. Water and solutes can cross the epithelium either between the cells (paracellular) or through the cell (transcellular). The overall electrical structure depicted, with a net positive charge along the apical side of the membrane forms the basis for epithelia electrical models discussed below.

While epithelia normally maintain their intracellular $Na^+$ concentration within a narrow range, cancer cells typically exhibit cytoplasmic $[Na^+]/[K^+]$ ratios that are three to five times greater than healthy epithelial cells. This is one explanation for the electrical depolarization that is observed in malignant or premalignant tissue, and may reflect the loss of $Na^+$ or $K^+$ gradients across the cell membrane. In addition to depolarization of the cell membrane, there may be a decrease in electrogenic $Na^{30}$ transport and activation of nonelectrogenic transporters during the development of epithelial malignancies. These changes contribute to the electrical differentiation between healthy and diseased tissue. As disease states such as cancer progress, they produce local changes in vascularization, water content, and cell division rate. These and other effects of the disease further alter the ionic concentrations in the tissue, which can be measured at the skin surface and within the neoplastic tissues. Other local effects, such as distortions in biologically closed circuits, may also occur.

It is worth recognizing that such effects do not occur uniformly throughout the diseased tissue. As a tumor grows and differentiates, it may show large variations in vascularity, water content, and cell division rate, and hence large variations in its electromagnetic character depending on where examination occurs. In addition to the previously noted electropotential changes, vascularity, water content and local increase in cellularity (i.e., more membranes) changes the manner in which induced currents would travel through the tissue and tumors. Tissue conductivity and membrane electrical storage capacity will be further defined. The electromagnetic properties at the core of the tumor (which may be necrotic) are likely to be very different from the electromagnetic properties at the margins of the tumor (which more probably contain the most metabolically active cells). Also, the tumor may not respond significantly to growth factors, while the enzymes and growth factors produced may significantly affect normal cells surrounding the tumor. It is thus desirable for a complete evaluation and diagnosis of tissue to make electrical measurements at a plurality of sites at and near the diseased area.

2.4. Measurement Techniques for Bioelectrical Parameters

In order to measure the electrical properties of tissue or an organ, the baseline electrical potential can be noted or a current I may be applied. The electrical system of the tissue is governed by Ohm's law, which may be written as V=IR, where V is the difference in electric potential across the tissue system and R is the resistance of the tissue system. When the epithelium becomes malignant, the electrical potential V and the resistance R are altered, thereby affecting the electrical characteristics of the tissue system; in general, both of these electrical parameters are measurable. Without intact membranes, dead tissue would be purely resistive. Live tissue thus needs to account for the complex alteration of resistance by intact membranes. Therefore, the complex electrical impedance Z of the tissue system may be measured in relation to the tissue resistance and membrane reactance, both of which vary according to the frequency of the applied current:

$$Z \equiv R + j(\omega L - 1/\omega C).$$

In this relationship, j is $\sqrt{-1}$, L is the inductance of the tissue system, C is the capacitance of the tissue system, and $\omega = v/2\pi$ is the angular frequency of the applied current [$I \propto e^{j\omega t}$]. The real part of the impedance is equal to the resistance, $\Re(Z)=R$, and the imaginary part of the impedance is equal to the reactance, $\Im(Z)=\omega L - 1/\omega C \equiv X$. It is thus apparent that when the phase of the voltage response relative to the applied current is zero, i.e. $\Phi=0$, the impedance of the tissue is equivalent to the resistance: Z=R. When the phase shift of the current lags behind, i.e. $\Phi=0$, the tissue response is inductive. Conversely, the tissue is more capacitive when $\Phi>0$. Tissues thus have characteristic electrical properties according to the frequency changes of the applied current.

Most previous methods for using potentials measured at the surface of a living organism are predicated on an overly simplistic hypothesis. Such methods operate on the basis that a disease state is indicated by a negative polarity with respect to a reference voltage measured at another site on the body while normal states are indicated by positive polarity with respect to the reference voltage. This hypothesis is inconsistent with the need explicated above for a plurality of measurements to obtain a reliable diagnosis. Even in prior-art devices that use multiple electrodes, their signals have merely been averaged so that a diagnostic determination is made from the polarity of a single average signal.

One prior-art device ("the Biofield device") that improves on this method is described in U.S. Pat. No. 5,823,957. The device described there operates by measuring skin surface electrical potentials with a plurality of electrodes that are sufficiently sensitive to detect 2-4 mV regions of depolarization. Measurements are taken concurrently from each of the electrodes but without distinct integration of any time-related phenomena. The measurements are then analyzed by calculating electric potential differentials between average readings of different electrodes. Although the data acquisition interval may be less than one minute, a ten-minute equilibration is needed in order to allow the sensitive electrodes to stabilize with skin ionic fluxes.

To detect disease states in the human breast, the Biofield device calculates electric potentials both within the involved breast and between the involved breast and contralateral breast. One disadvantage is that these measurements are affected by factors irrelevant to the diagnosis and which make such a diagnosis more uncertain. For example, the measured electrical potentials may vary according to where the patient is in her menstrual cycle, her diet, and the time of day, in addition to whether there is underlying abnormal proliferation or cancer. The placement of the electrodes is also highly dependent on the investigator or technician localizing the lesion by palpation or estimating the closest surface trajectory based on mammographic triangulation. The uncertainty for nonpalpable lesions is thus significant, and it is desirable to have a method and apparatus that are not so highly dependent on the operator's skill. More importantly, curable early stage breast cancer is frequently non-palpable. Reliable correlation with mammogram is thus greatly needed to improve mammographic screening performances.

Another prior-art device ("the TransScan device") is described in U.S. Pat. No. 5,810,742. This device generates an impedance image from capacitance and conductance data obtained from multiple elements in a sensing probe placed over the breast. Impedance mapping is calculated from a range of frequencies from a received signal that was pulsed (at about one volt) from a cylindrical device held in the contralateral hand. The sensitivity of impedance mapping for detecting cancer is a function of the frequency, and at particular frequencies becomes characteristic of the tissue being imaged. A two-dimensional image is reconstructed from the analysis of the capacitance and conductivity measurements (see FIG. 14 of U.S. Pat. No. 5,810,742).

It is currently unknown what effect various extraneous factors such as those enumerated above have on the results produced using the TransScan impedance-measuring technique. The amplitude of capacitance and conductivity graphs are converted into relative brightness for a gray scale spectrum. Unfortunately, potentially discriminant digital data is thus converted to an analog image for operator interpretation and discrimination. Even more problematic is that there is a significant dependency on the skill of the operator to recognize and identify image artifacts during scanning. Rather than digital separation and potential elimination, artifacts from underlying ribs and other structures thus detract from an operator's evaluation. Similar to the use of real-time ultrasound readings, the reliability of the TransScan device is intimately tied with the ability of the operator to produce consistent, clinically meaningful results.

Another prior-art bioimpedance device that is intended exclusively for use in cardiac monitoring is the BioZ, marketed by CardioDynamics Int'l Corp. [http://www.bioz.com]. This device functions by using a total-thoracic approach that correlates blood volume with the inverse relationship to resistance. Two dual electrodes are placed on each side of a patient's neck and chest and an electrical signal is transmitted through the thorax. From the assumption that the most conductive path in the thorax is along the aorta, the BioZ uses changes in resistance to deduce hemodynamic parameters. Because of this limitation, the principles on which the device is based are not applicable for analysis of other systems. Furthermore, the device is not well suited to an increase in the number of potential current pathways since even such an increase would not improve the analysis.

2.5. Physical and Mathematical Modeling

To correlate the results of impedance measurements with appropriate tissue characterization, a valid physical and mathematical model of the electromagnetic character of the tissue is needed. In the prior art, the tissue has been approximated with lumped-element models. As a representation of living tissue, such models are rather crude and their actual usefulness is correspondingly limited. Although a continuum approximation was proposed for an impedance analysis of epithelium in one case [Richard J. Davies et al., *Epithelial Impedance Analysis in Experimentally Induced Colon Cancer*, Biophys. J., 52, 783 (1987)], the model was not actually used to analyze data. Furthermore, ionic transport through tissue has consistently been assumed to be linear in such models, and there are no studies of tissue nonlinearity as a separate characteristic signature.

The lumped-element models have a number of limitations that are either inherent or have been introduced as a result of simplifying assumptions. For example, the general strategy used in constructing a lumped-element model has been to assign a single resistance $R_i$ to the intracellular current flow through the epithelium, and to assign a separate single resistance $R_e$ to the extracellular current flow along the epithelium together with a capacitance $C_m$ associated with the component of the ionic current flow that does not go across the epithelium [see generally T. Morimoto et al., *A Study of the Electrical Bio-impedance of tumors*, J. Invest. Surg., 6, 25 (1993)]. No serious attempt has been made to account for the random orientations of the epithelia and the resulting complex current paths associated with in vivo measurements.

A further weakness with lumped-element models is that only the capacitive reactance has been considered. This simplifying assumption has been made despite a clear showing that reactance increases with frequency over a distinct range of frequencies 1-20 MHZ. This inductive reactance is significant in characterizing the electrical properties of the tissue and should properly be considered For example, for unimpaired ionic current flow, such as that associated with currents along the epithelium or in bulk fluids including saline and blood, the reactance is expected to be primarily inductive. When the reactance increases with frequency, then the system is displaying an induction response. Conversely, current flow that consists of heavy ions that do not transport across the epithelium will result in a reactance where the capacitive component dominates over the inductive component.

Hence, it is necessary that a realistic model of tissue electrical characteristics account for both the capacitive and inductive character of the reactance. Proper characterization of tissue thus requires that both the capacitive and inductive components of the reactance be measured as functions of the frequency, drive level, and relative orientation with respect to the current drive. There is thus a need for a method and apparatus for coupling such measurements with a continuum model of different tissue types to serve as an indicator of the electrical behavior of epithelium, and hence, as a sensitive and early detector of cancer.

3. OBJECTS OF THE INVENTION

It is thus a first object of the invention to provide a method and apparatus for using bioimpedance measurements in the detection and characterization of medical pathologies, including cancer.

It is a second object to provide a method and apparatus that makes use of any information available from complex impedance measurements, including resistive, capacitive, and inductive components.

It is a third object to provide a method and apparatus that is used both in isolation and in conjunction with other methods and apparatuses for imaging biological systems.

It is a fourth object to provide a method and apparatus that functions automatically with a trained computational evaluation system to analyze the full complex impedance measurements and ascertain different tissue types.

It is a fifth object to provide a method and apparatus with versatile applications: it is an object to provide a method and apparatus that have applications in the diagnosis of oncologic pathologies in numerous tissues in human and animal bodies and in the diagnosis of other pathologies in the cardiac, pulmonary, neurologic, and skeletal systems; it is a further object to provide a method useful in the assessment of the efficacy of medical therapies and in screening for abnormal proliferative tissue in humans and animals; it is also an object to provide an apparatus with which bioimpedance measurements are taken while a practitioner palpates tissue or examines tissue intraoperatively; it is an additional object to provide an apparatus used to analyze pathology specimens; and it is still a further object to provide improved electrocardiograph, electroencephalograph, and electromyograph devices that make use of the complex bioimpedance data.

4. SUMMARY OF THE INVENTION

In a first embodiment, the invention provides an apparatus for the detection and characterization of one or more medical pathologies within an object under study. The apparatus comprises a current source adapted to provide current with a predetermined current waveform and disposed so as to be capable of electrically stimulating the object. The apparatus further comprises a plurality of electrodes, each capable of measuring a voltage, disposed to receive current from the object, and comprises means for controlling the current source and electrodes. The apparatus also comprises a device coupled to the electrodes and configured to calculate a complex impedance for each drive path defined by the current source and electrodes, to construct a multidimensional representation of the electrical characteristics within a region of the object using the calculated complex impedances, and to detect and characterize the pathologies from the multidimensional representation.

The apparatus preferably comprises a plurality of current routings sources. It is also preferred that the plurality of electrodes be switched between at least one device that is used as a current source and as a current sink. Any number of electrodes greater than two may be used. The electrodes may be disposed on a glove that comprises a position sensor. The current waveform is preferably sinusoidal, but alternatively has a profile selected from the group consisting of square, triangular, ramp, pulse, and sink. The current waveform also preferably comprises an oscillation frequency between 2 Hz and 2 MHz. The magnitude of the current waveform is preferably between 10 nA and 1 mA. The apparatus also preferably comprises means for reducing electrical noise, this means preferably being a digital-signal-processor-based lock-in amplifier.

The device coupled to the apparatus preferably also calculates complex impedance derivatives with respect to frequency for each current path. The construction of the multi-dimensional representation of the electrical characteristics is preferably done by solving a continuum electrical model. Such a model preferably comprises Zener-diode elements with reverse break-down potential similar to the cell polarization potential, whereby the model incorporates nonlinearities. The model also preferably comprises an inductive element. In one embodiment, the model comprises an inductive element, a capacitive element, a resistive element, and Zener diode elements. The multidimensional representation may be a ten-dimensional representation, and where the object under study is human or animal tissue, the ten dimensions correspond to differential cell-membrane capacitance, intracellular-fluid differential resistance, extracellular differential resistance, differential surface membrane inductance, and a range of variation for each of these four quantities, in addition to the amplitude of the current source and frequency of the current waveform. Preferably, the four ranges are contracted with each of the four respective quantities, resulting in a six-dimensional representation. It is also preferable that the device project the multidimensional representation onto a plurality of three-dimensional spaces and selects one of those three-dimensional spaces for display. The device also preferably uses a trained evaluation system to perform the step of detecting and characterizing the medical pathologies. Such a trained evaluation system may comprise, without limitation, an expert system or neural net, or use stochastic optimization or a genetic algorithm.

The object under study preferably comprises a plurality of human or animal organs or tissues. Such organs or tissues may comprise, without limitation, a human breast, a human prostate, a human kidney, a human lung, a section of a human alimentary canal, a human liver, lymphatic tissue, a human heart, or brain. One application of the apparatus for such tissues is where the medical pathology is oncologic, i.e. there is proliferative tissue or cancer within the object. It is also preferable that the apparatus comprise means for generating a compression wave within the object. Such a compression wave may by generated by ultrasound, palpation, or any other means.

The apparatus also preferably comprises a radiation source adapted to emit radiation within a predetermined frequency or at a predetermined frequency onto a volume within the object under study and a radiation detector disposed to receive radiation scattered by the volume. In such case, the device further performs the step of using data provided by the radiation detector in combination with the complex impedances to further characterize medical pathologies within the volume. Preferably, the radiation source and detector are an ultrasound source and detector.

The ultrasound source and detector are preferably fabricated in a single unit. The data provided by the radiation detector are preferably digitized, and preferably digitized at a rate greater than or equal to 30 kHz. Where the ultrasound source emits monochromatic radiation, the detector may be configured to detect only scattered radiation that is at a predetermined phase relationship with the monochromatic radiation or may be configured to detect any radiation that is detuned from the monochromatic radiation. The ultrasound source may also be configured to emit chirped radiation.

The coupling of complex impedance measurements with ultrasound measurements finds a number of applications, many of which are non-oncologic. One such application is where the medical pathology is a cardiac pathology, such as a valvular dysfunction. In such case, the apparatus preferably also comprises a standard electrocardiograph. Another application is where the medical pathology is a vascular pathology. For such application, the apparatus preferably further comprises means for imposing a concentrated magnetic field within the object under study. It is also preferred that the apparatus comprise means for scanning the concentrated magnetic field across the object. Yet another application is where the medical pathology is a pulmonary pathology, such as a bronchus spasm, pneumothorax, regional hyperinflation, consolidation, or a neoplasm. Still a further application is where the medical pathology comprises a neurological pathology. For such application, the apparatus preferably further comprises a standard electroencephalograph. Still another application is where the medical pathology comprises a neuromuscular pathology. For such application, the apparatus preferably further comprises a standard electromyograph. Other applications include the characterization of skeletal pathologies such as a bone fracture.

The apparatus also finds pathology applications where it further comprises a container for holding the object under study with the current source and electrodes disposed within the walls of the container. In such cases, the object under study may be, for example and without limitation, a cell culture, a surgical tissue specimen, or a laboratory animal. Examples of such a container include, without limitation, culture wells in a plate, a test tube, and a Petri dish. Preferably, the contain comprises a hemispherically shaped bottom. It is also preferable that the container contain an electrically conductive fluid. Such fluid preferably has a specific gravity greater than the object under study. A specific gravity greater than or equal to 1.2 is sufficient for most applications described envisaged.

The apparatus may alternatively comprise a contact instrument that comprises the current source and electrodes, all of which are disposed on one surface of the instrument. In such a case, evaluation of the object under study may be performed by bringing the instrument into contact with the object. Multiple needles with electrodes at the tip can pierce living or excised tissues, measuring Z at multiple different levels during penetration.

In a second embodiment, the invention also provides an apparatus for the detection and characterization of one or more medical pathologies within an object under study. The apparatus comprises a current source adapted to provide current with a predetermined current waveform, a plurality of electrodes, each capable of measuring a voltage, means for controlling the current source and plurality of electrodes, and a device coupled to said plurality of electrodes and configured to analyze data received from said plurality of electrodes to detect and characterize such one or medical pathologies. The predetermined current waveform is preferably sinusoidal, but may also have a profile selected from the group consisting of square, triangular, ramp, pulse, and sinc. The predetermined current waveform preferably comprises an oscillation frequency between 2 Hz and 2 MHz. The magnitude of the predetermined current waveform is preferably between 10 nA and 1 mA.

A third embodiment of the invention also provides an apparatus for detection and characterization of one or more medical pathologies within an object under study. The apparatus comprises a current source, a plurality of electrodes, means for controlling such current source and said plurality of electrodes to produce and receive current, and a device coupled to said plurality of electrodes. The device is configured to calculate a plurality of complex impedances, each of which corresponds to a current drive path defined by the current source and an electrode, and to analyze the complex impedances to detect and characterize such one or more medical pathologies. Preferably, the device is further configured to construct a multidimensional representation of the electrical characteristics of the object using the complex impedances. Preferably, the device also projects such a multidimensional representation into a plurality of three-dimensional spaces.

An apparatus for the detection and characterization of one or more medical pathologies within an object under study is also provided by a fourth embodiment of the invention. The apparatus comprises a current source, a plurality of electrodes, means for controlling such current source and said plurality of electrodes, and a device coupled to the electrodes and configured to analyze data received from them to detect and characterize such one or medical pathologies by solving a continuum electrical model. The solution of the continuum electrical model results in the construction of a multidimensional representation of the electrical characteristics of the object under study. Preferably, the continuum electrical model comprises Zener-diode elements, whereby nonlinearities are incorporated into the model. The model also preferably comprises inductive elements. Most preferably, the model incorporates an inductive element, a capacitive element, a resistive element, and Zener diode elements.

In a fifth embodiment, the invention again provides an apparatus for the detection and characterization of one or more medical pathologies. The apparatus comprises a current source, a plurality of electrodes, means for controlling the current source and electrodes, and a device coupled to the electrodes and configured to analyze data received from them to detect and characterize such one or medical pathologies. In this embodiment, the electrodes are disposed on at least one glove. Preferably, the glove also comprises a position sensor.

In a sixth embodiment, the invention provides a method for the detection and characterization of one or more medical pathologies within an object under study. The method of the invention comprises the steps of: (a) stimulating such object electrically with a current source adapted to provide current with a predetermined current waveform; (b) measuring a plurality of voltages with a plurality of electrodes disposed relative to such object for receiving current from such object; (c) calculating a plurality of complex impedances from said plurality of voltages, each of said plurality of complex impedances corresponding to a current drive path defined by said current source and one of said plurality of electrodes; (d) constructing a multidimensional representation of the electrical characteristics of a region within such object using said plurality of complex impedances; and (e) detecting and characterizing such one or more medical pathologies within such object from said multidimensional representation.

The method preferably uses a plurality of current sources. It is also preferred that the plurality of electrodes include at least one set that is used both as a current source and as a current sink. Any number of electrodes greater than two may be used. The electrodes may be disposed on a glove or linked on bands, or on a flexible membrane. The current waveform is preferably sinusoidal, but alternatively has a profile selected from the group consisting of square, triangular, ramp, pulse, and sinc. The current waveform also preferably comprises an oscillation frequency between 2 Hz and 2 MHz. The magnitude of the current waveform is preferably between 10 nA and 1 mA. The method also preferably reduces electrical noise, preferably with a digital-signal-processor-based lock-in amplifier.

The method also preferably comprises calculating complex impedance derivatives with respect to frequency for each current path. The construction of the multidimensional representation of the electrical characteristics is preferably done by solving a continuum electrical model. Such a model preferably comprises Zener-diode elements, whereby the model incorporates nonlinearities. The model also preferably comprises an inductive element. In one embodiment, the model comprises an inductive element, a capacitive element, a resistive element, and Zener diode elements. The multidimensional representation may be a ten-dimensional representation, and where the object under study is human or animal tissue, the ten dimensions correspond to differential cell-membrane capacitance, intracellular-fluid differential resistance, extracellular differential resistance, differential surface membrane inductance, and a range of variation for each of these four quantities, in addition to the amplitude of the current source and frequency of the current waveform. Preferably, the four ranges are contracted with each of the four respective quantities, resulting in a six-dimensional representation. It is also preferable that the method comprise a step of projecting the multidimensional representation onto a plurality of three-dimensional spaces and selecting one of those three-dimensional spaces for display. The method also preferably uses a trained evaluation system to perform the step of detecting and characterizing the medical pathologies. Such a trained evaluation system may comprise, without limitation, an expert system or neural net, or use stochastic optimization or a genetic algorithm.

The object under study preferably comprises a plurality of human or animal organs or tissues. Such tissues may comprise, without limitation, a human breast, a human prostate, a human kidney, a human lung, a section of a human alimentary canal, a human liver, lymphatic tissue (heart and brain). One application of the method for such tissues is where the medical pathology is oncologic, i.e. there is proliferative tissue or cancer within the object. It is also preferable that the method comprise generating a compression wave within the object. Such a compression wave may by generated by ultrasound, palpation, or any other means. In other applications, the object under study comprises a surgical specimen or laboratory animal.

The method also preferably comprises irradiating a volume within the object under study using a radiation source, receiving radiation scattered by the volume with a plurality of radiation detectors, and using the data received from the radiation detectors in combination with the complex impedances to further characterize the medical pathologies. Preferably, the radiation source and detector are an ultrasound source and detector.

The ultrasound source and detector are preferably fabricated in a single unit. The data provided by the radiation detector are preferably digitized, and preferably digitized at a rate greater than or equal to 30 kHz. Where the ultrasound source emits monochromatic radiation, the detector may be configured to detect only scattered radiation that is at a predetermined phase relationship with the monochromatic radiation or may be configured to detect any radiation that is detuned from the monochromatic radiation. The ultrasound source may also be configured to emit chirped radiation.

As above, the coupling of complex impedance measurements with ultrasound measurements finds a number of applications, many of which are non-oncologic. One such application is where the medical pathology is a cardiac pathology, such as a valvular dysfunction. Another application is where the medical pathology is a vascular pathology. For such application, the method preferably further comprises imposing a concentrated magnetic field within the object under study. It is also preferred that the method comprise scanning the concentrated magnetic field across the object. Yet another application is where the medical pathology is a pulmonary pathology, such as a bronchus spasm, Stein Ron Chi, consolidation, or a neoplasm. Still a further application is where the medical pathology comprises a neurological pathology. Still another application is where the medical pathology comprises a neuromuscular pathology. Other applications include the characterization of skeletal pathologies such as a bone fracture.

The method is also preferably coupled with at least one supplementary technique for analyzing the object. Use of the supplementary technique may be before or after the step of detecting and characterizing the object under study using complex impedance results. Examples of the supplementary technique include, without limitation, x-ray imaging, mammography, computed tomography, magnetic resonance imaging, ultrasound, nuclear medicine, single-photon emission computed tomography, and positron-emission tomography.

In a seventh embodiment, the invention provides a method for assessing the efficacy of medical therapy comprising the steps of: (a) characterizing a medical pathology within an organ or tissue of each of a plurality of subjects, said step of characterizing comprising the substeps of: (i) stimulating such organ or tissue electrically with a current source adapted to provide current with a predetermined current waveform; (ii) measuring a plurality of voltages with a plurality of electrodes disposed relative to such tissue for receiving current from such tissue; (iii) calculating a plurality of complex impedances from said plurality of voltages, each of said plurality of complex impedances corresponding to a current drive path defined by said current source and one of said plurality of electrodes; (iv) constructing a multidimensional representation of the electrical characteristics of such tissue using said plurality of complex impedances; and (v) characterizing said medical pathology within such tissue from said multidimensional representation; (b) applying said medical therapy; (c) repeating said step of characterizing on each of said plurality of subjects after applying said medical therapy; and (d) evaluating the effect of said medical therapy statistically among said plurality of subjects by comparing a characterization of said medical pathology resulting from said step (a)(v) of characterizing with a characterization of said medical pathology resulting from said step (c) of repeating. Preferably, the medical therapy is a pharmacological treatment. The medical pathology is preferably a precancerous condition. Examples of tissue include, without limitation, breast tissue, prostate tissue, kidney tissue, lung tissue, alimentary canal tissue, liver tissue, and lymphatic tissue. The method also preferably includes the step of positioning the electrodes equivalently on each of the subjects. This is preferably done by having the electrodes fixed on an adhesive pad.

The invention also provides, in an eighth embodiment, a method for screening a patient for abnormal tissue comprising the steps of: (a) characterizing a volume of tissue within said patient, said step of characterizing comprising the substeps of: (i) stimulating such volume electrically with a current source adapted to provide current with a predetermined current waveform; (ii) measuring a plurality of voltages with a plurality of electrodes disposed relative to such volume for receiving current from such volume; (iii) calculating a plurality of complex impedances from said plurality of voltages, each of said plurality of complex impedances corresponding to a current drive path defined by said current source and one of said plurality of electrodes; (iv) constructing a multidimensional representation of the electrical characteristics of such volume using said plurality of complex impedances; and (v) characterizing such tissue from said multidimensional representation; and (b) comparing the characterization of such tissue with a reference tissue characterization. It is preferred that the method further comprise the step of localizing the volume with a supplementary technique. Examples of supplementary techniques include, without limitation, x-ray imaging, mammography, computed tomography, magnetic resonance imaging, ultrasound, nuclear medicine, single-photon emission computed tomography, and positron-emission tomography. The method also preferably comprises the step of performing a biopsy on the volume. The reference tissue may be determined from a previous tissue characterization of the patient or from a characterization derived from a plurality of tissue characterizations for a population.

The invention, in a ninth embodiment, provides a method for the detection and characterization of one or more medical pathologies within an object under study comprising: (a) stimulating such object electrically with a current source adapted to provide current with a predetermined current waveform; (b) measuring a plurality of voltages with a plurality of electrodes disposed relative to such object for receiving current from such object; and (c) analyzing data received from said plurality of electrodes to detect and characterize such one or more medical pathologies. The predetermined current waveform is preferably sinusoidal. Other profiles for the predetermined current waveform include, without limitation, square, triangular, ramp, pulse, and sinc. The oscillation frequency of the predetermined current waveform is preferably between 2 Hz and 2 MHz. The magnitude of the predetermined current waveform is preferably between 10 nA and 1 mA.

In a tenth embodiment, the invention provides a method for detection and characterization of one or more medical pathologies within an object under study comprising the steps of: (a) stimulating such object electrically with a current source; (b) measuring a plurality of voltages with a plurality of electrodes disposed relative to such object for receiving current from such object; (c) calculating a plurality of complex impedances, each of said plurality of complex impedances corresponding to a current drive path defined by said current source and one of said plurality of electrodes; and (d) analyzing said plurality of complex impedances to detect and characterize such one or more medical pathologies. Preferably, the method further comprises the step of constructing a multidimensional representation of the electrical characteristics of the object using the complex impedances. The method also preferably comprises projecting the multidimensional representation into a plurality of three-dimensional spaces.

In an eleventh embodiment, the invention provides a method for detection and characterization of one or more medical pathologies within an object under study comprising: (a) stimulating such object electrically with a current source; (b) measuring a plurality of voltages with a plurality of electrodes disposed relative to such object for receiving current from such object; and (c) analyzing data received from said plurality of electrodes to detect and characterize such one or more medical pathologies by solving a continuum electrical model to construct a multidimensional representation of the electrical characteristics of said object under study. The continuum electrical model preferably comprises Zener-diode elements, whereby nonlinearities are incorporated into the model. The model also preferably comprises an inductive element. Most preferably, the continuum electrical model comprises an inductive element, a capacitive element, a resistive element, and Zener-diode elements.

In a twelfth embodiment, the invention provides a method for detection and characterization of one or more medical pathologies within an object under study comprising: (a) stimulating such object electrically with a current source; (b) measuring a plurality of voltages with a plurality of electrodes; and (c) analyzing said plurality of complex impedances to detect and characterize such one or more medical pathologies; wherein said plurality of electrodes are disposed on at least one glove, whereby said plurality of electrodes are disposed relative to such object to receive current from such object when said at least one glove is in contact with such object. Preferably, a position sensor is further disposed on the glove, a flexible membrane to attach to skin anywhere, or a ring of electrodes on elastic bands.

4.1 ADVANTAGES OF THE INVENTION

It is thus a first advantage of the invention that a method and apparatus are provided for the detection and characterization of medical pathologies using bioimpedance measurements that make use of the complex impedance, including resistive, capacitive, and inductive components.

It is a second advantage of the invention that a method and apparatus are provided that use a current waveform, rather than a voltage waveform, to stimulate electrical currents within an object under study in order to detect and characterize medical pathologies with the use of bioimpedance measurements.

It is a third advantage of the invention that a method and apparatus are provided for the detection and characterization of medical pathologies that make use of a continuum model of epithelial tissue to analyze bioimpedance measurements.

It is a fourth advantage of the invention that a method and apparatus are provided for the detection and characterization of medical pathologies that make use of a model of epithelial tissue that contains nonlinearities in order to analyze bioimpedance measurements.

It is a fifth advantage of the invention that a method and apparatus are provided for the detection and characterization of medical pathologies that use electrodes positioned on gloves to collect bioimpedance data. This is advantageous because it permits a practitioner to palpate tissues as part of an evaluation and to perform intraoperative evaluations.

It is a sixth advantage of the invention that a method and apparatus are provided for the automatic detection and characterization of medical pathologies using a trained evaluation system to analyze bioimpedance measurements.

It is a seventh advantage of the invention that a method and apparatus are provided for the detection and characterization of medical pathologies in varied biological systems including, but not limited to, the breast, the prostate, the lung, the alimentary canal, the liver, and lymph tissue, etc.

It is an eighth advantage of the invention that an apparatus is provided for the detection and characterization of medical pathologies within cell cultures, surgical specimens, laboratory animals, and simulatation models using fixed elements for the collection of complex bioimpedance data with resistive, capacitive, and inductive components.

It is a ninth advantage of the invention that a method is provided for assessing the efficacy of medical therapies, including pharmacological therapies, using complex bioimpedance measurements with resistive, capacitive, and inductive components.

It is a tenth advantage of the invention that a method is provided for screening a patient for abnormal tissue through the use of complex bioimpedance measurements with resistive, capacitive, and inductive components.

It is an eleventh advantage of the invention that methods and apparatuses are provided for the detection and characterization of medical pathologies with a large number of biological applications, including oncologic, cardiac, vascular, pulmonary, neurological, and orthopedic applications.

It is a twelfth advantage of the invention that improved electrographic devices, including electrocardiographs, electroencephalographs, and electromyographs, are provided that make use of complex bioimpedance measurements with resistive, capacitive, and inductive components.

Each of these advantages is combined in various embodiments of the invention that exploit individual or multiple aspects of the invention to achieve various useful methods and apparatuses. Other advantages may occur to those of skill in the art after reading the detailed disclosure and figures. The invention is not limited to those advantages recited above, but encompasses all inherent advantages as well as those that would occur to those of skill in the art in light of the disclosure.

5. BRIEF DESCRIPTION OF THE DRAWINGS

FIG. 1 is a cross section of a portion of epithelial tissue illustrating the electrical gradients that exist in healthy tissue.

FIGS. 2(a-d) show the construction of various electrical models of the epithelium: In FIG. 2(a), a schematic representation of the epithelium illustrating the origin of the model elements is illustrated; in FIG. 2(b), the circuit for the simple prior-art lumped element model is shown; in FIG. 2(c), the circuit for a continuum model is illustrated using resistive elements—FIG. 2(c)(ii) shows the continuum model circuit with infinite elements and FIG. 2(c)(ii) shows an equivalent continuum model circuit; in FIG. 2(d), the circuit for the continuum model of the present invention is shown, using fill complex impedances and using nonlinear model elements.

FIG. 3 reproduces the three-dimensional distribution of impedance parameters $R_i$, $R_e$, and $C_m$ in breast diseases from Morimoto et al., J. Invest. Surg., 6, 25 (1993).

FIGS. 6(a-d) illustrate various embodiments of the invention in which electrodes are fixedly positioned in the walls of a container used for analysis of cell cultures, surgical specimens, and laboratory animals: FIG. 6(a) shows an embodiment in which electrodes are placed within culture wells on a culture plate; FIG. 6(b) shows an embodiment in which electrodes are placed within the walls of a test tube; FIG. 6(c) shows an embodiment in which electrodes are placed in the bottom plate of a Petri dish; FIG. 6(d) shows an embodiment in which electrodes are placed within the walls of a specimen container. For each embodiment, the positions of the electrodes are indicated by arrows.

Figure 7:
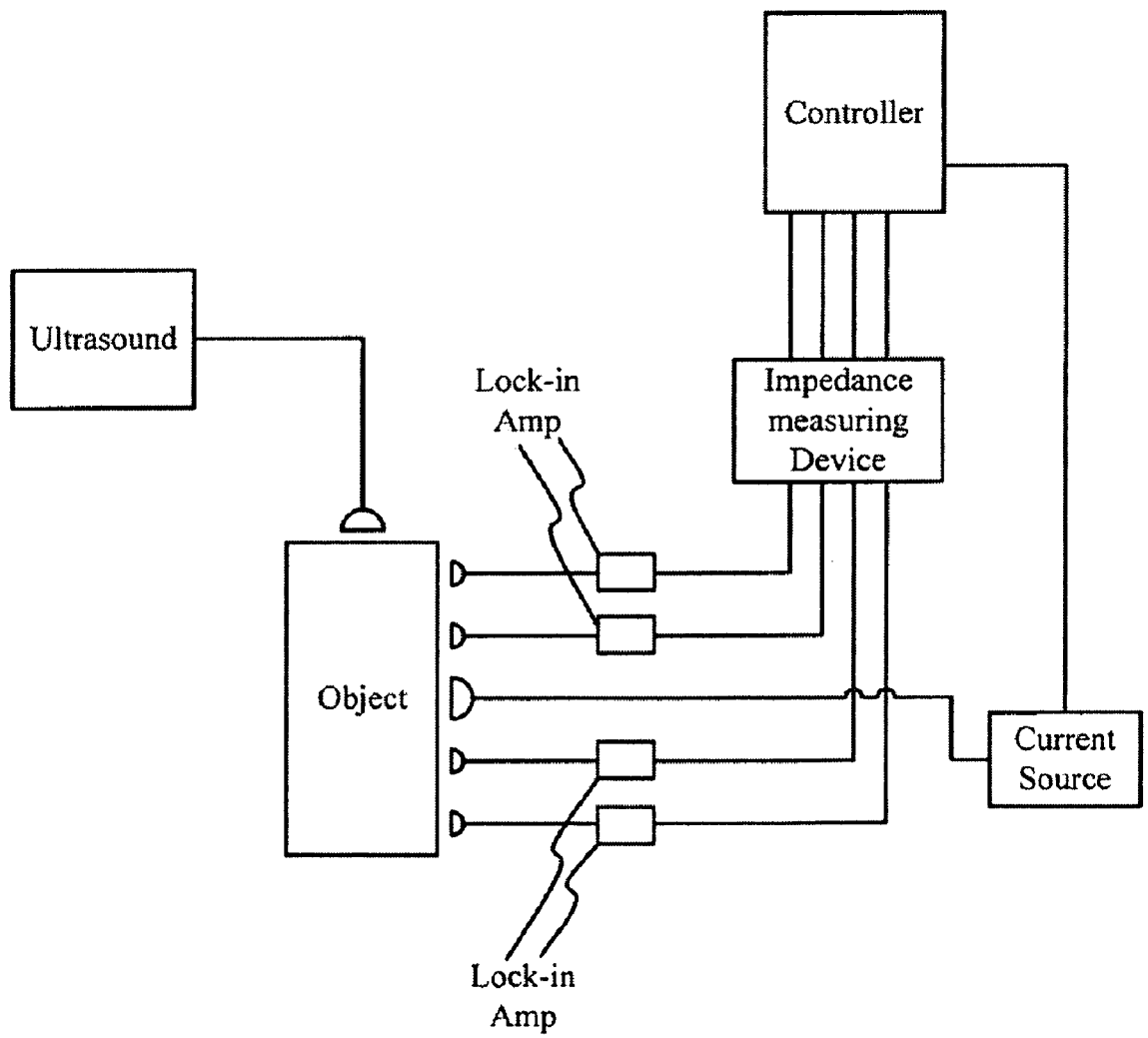

FIG. 7 illustrates a block diagram of an system for measuring complex impedances of an object according to one embodiment of the invention.

Figure 8:
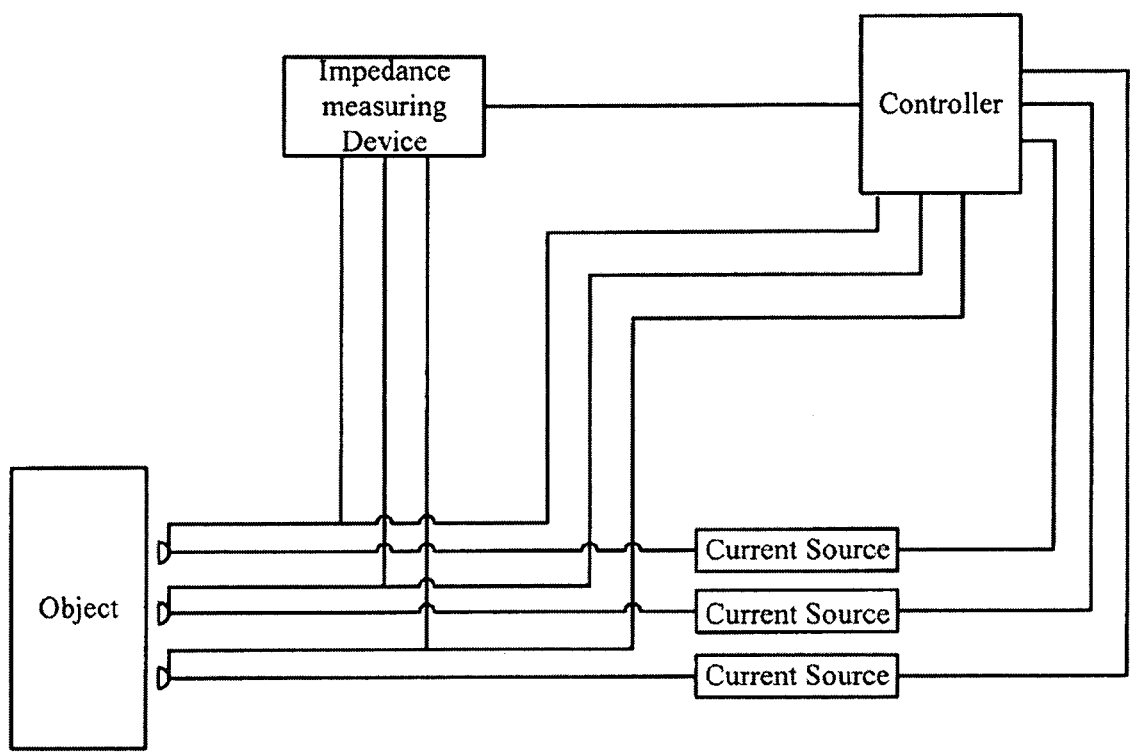

FIG. 8 illustrates a block diagram of an system for measuring complex impedances of an object according to another embodiment of the invention.

Figure 9:
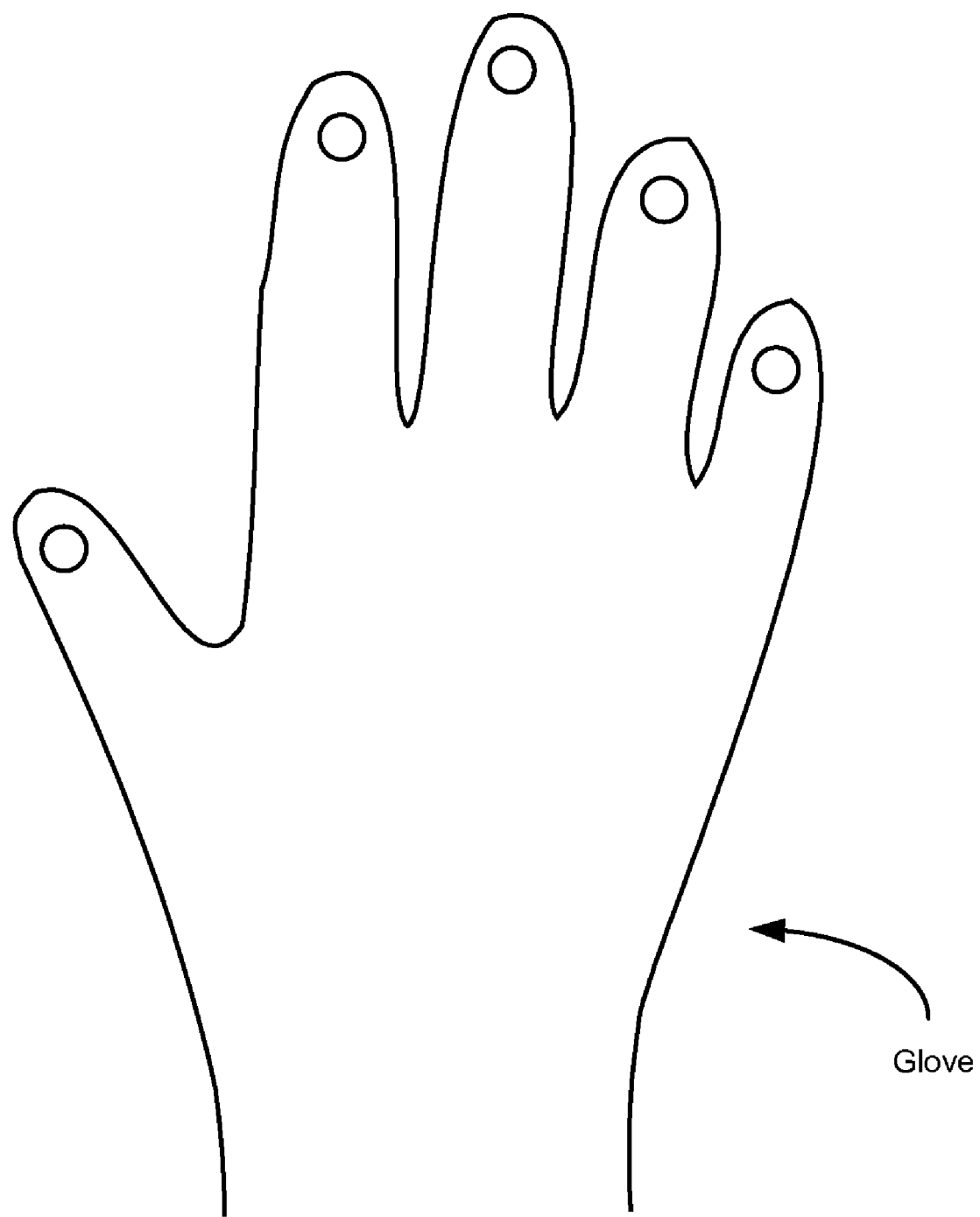

FIG. 9 shows a glove sensor system according to one embodiment of the invention.

Figure 10:
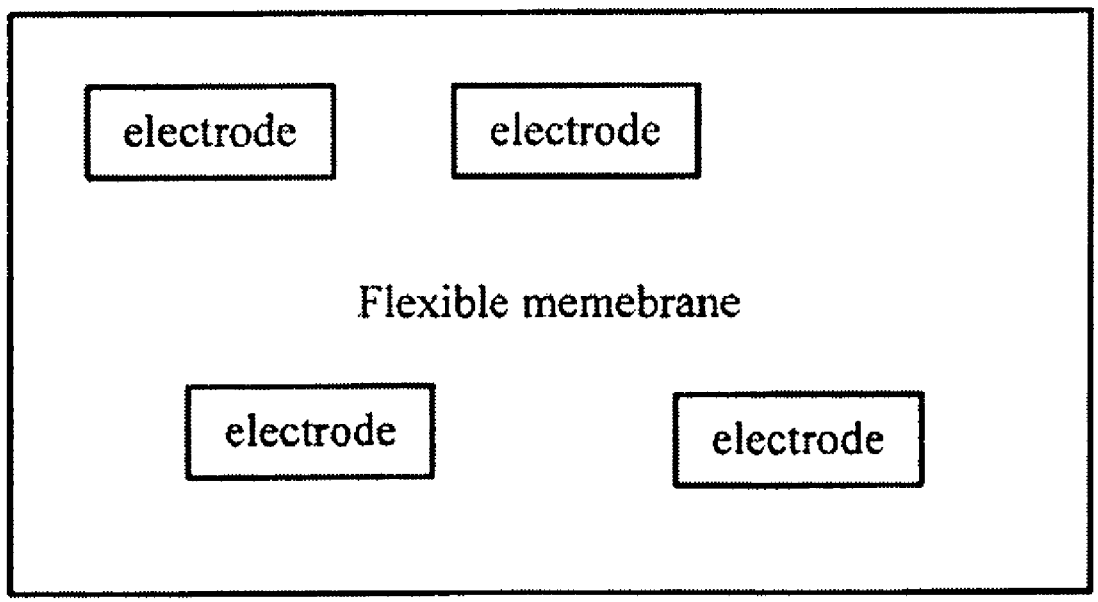

FIG. 10 shows a block diagram of a flexible membrane sensor system according to one embodiment of the invention.

Figure 11:
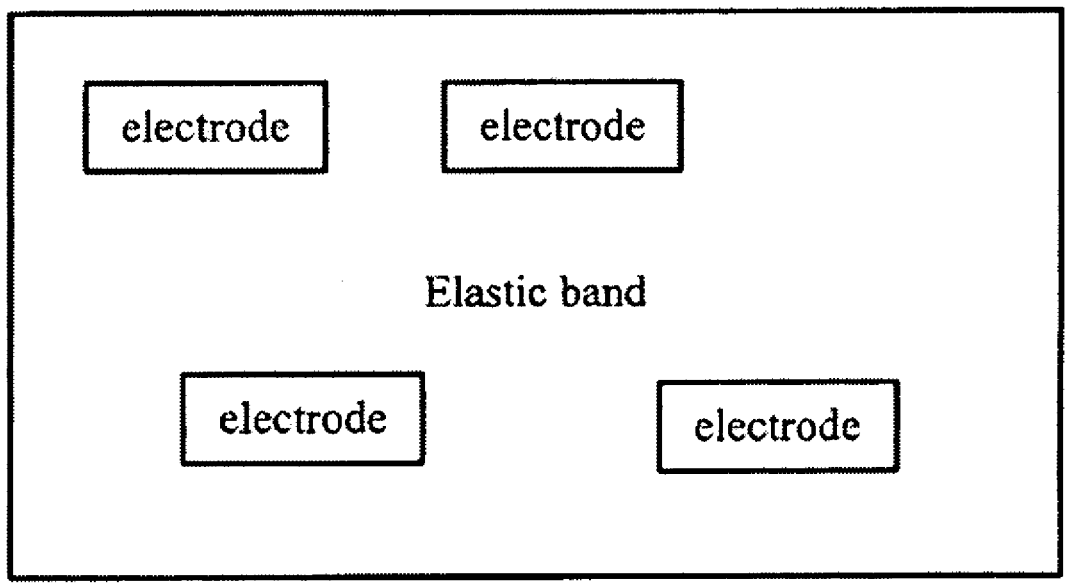

FIG. 11 shows a block diagram of an elastic band sensor system according to one embodiment of the invention.

Figure 12:
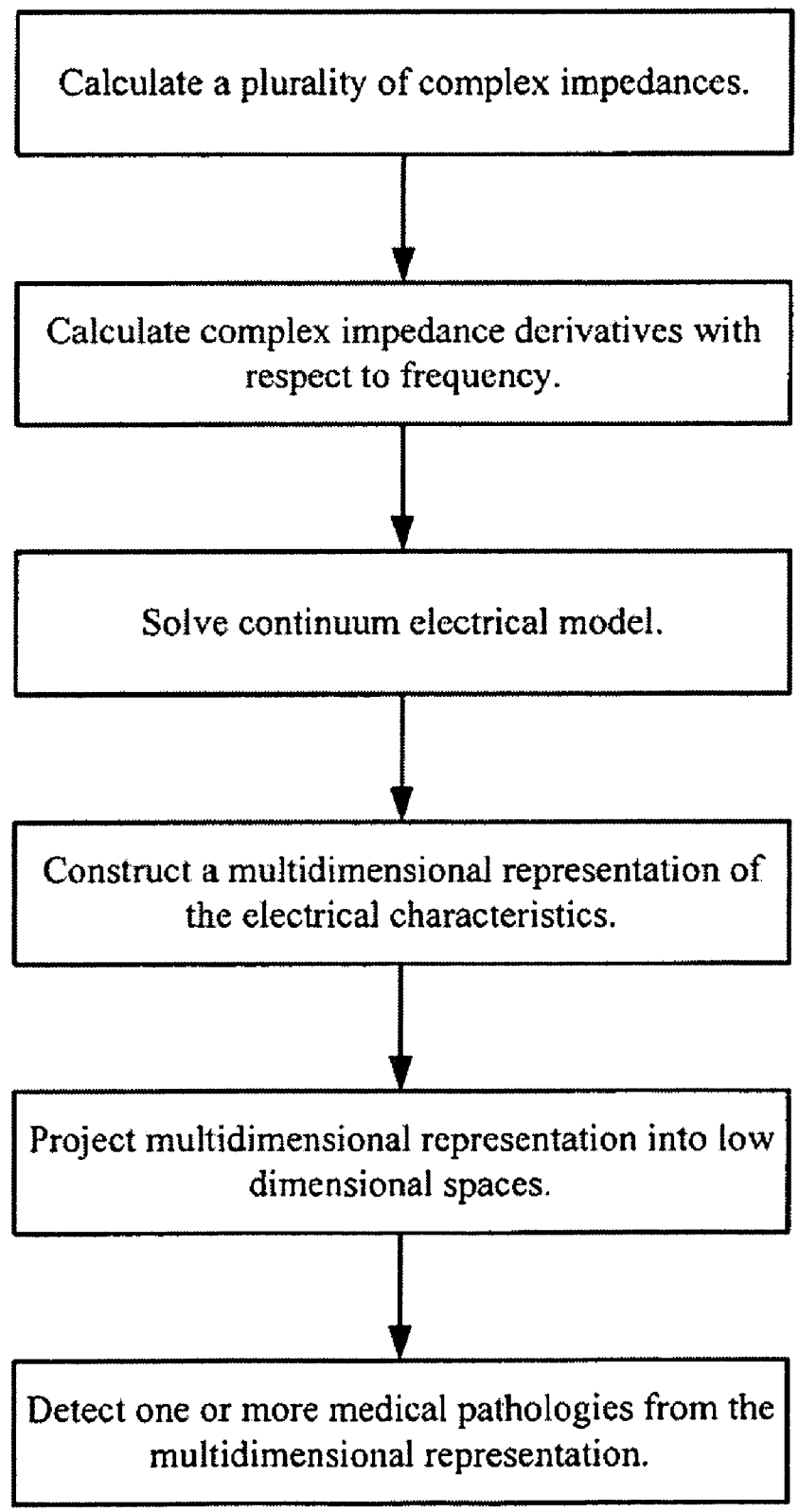

FIG. 12 shows a flowchart depicting a method for detection and characterization of one or more medical pathologies within an object under study according to one embodiment of the invention.

Figure 13:
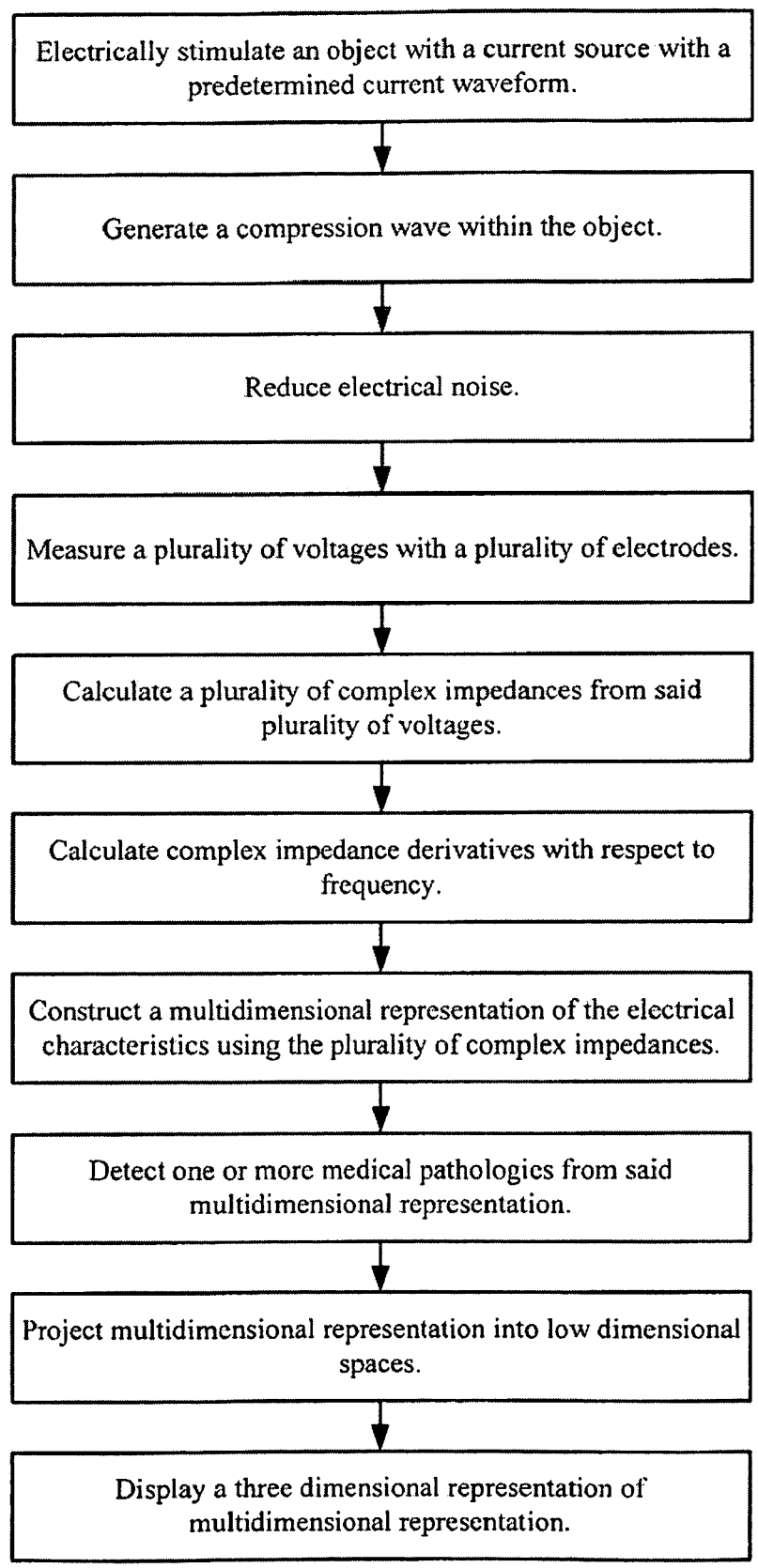

FIG. 13 shows another flowchart depicting a method for detection and characterization of one or more medical pathologies within an object under study according to one embodiment of the invention.

Figure 14:
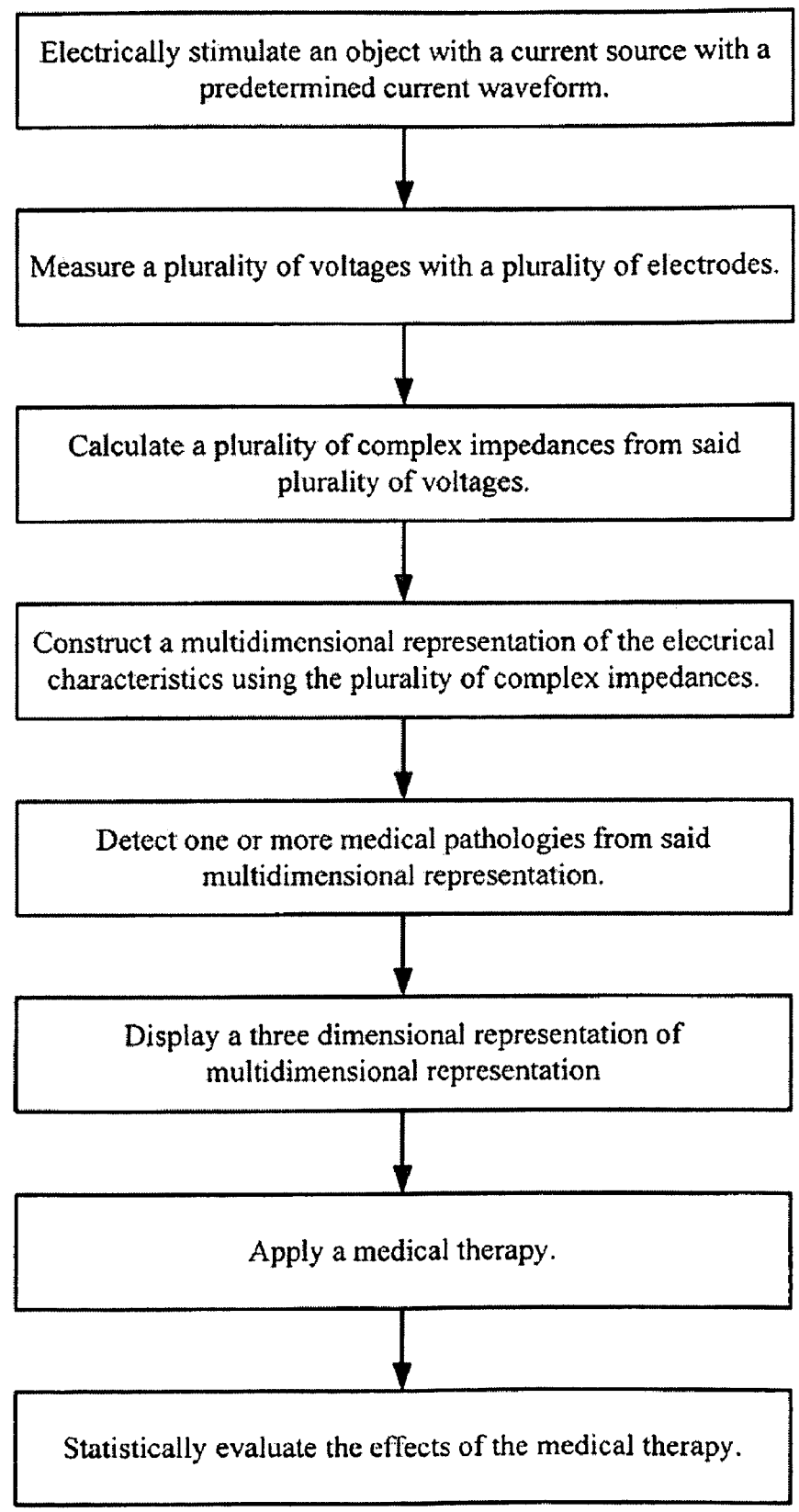

FIG. 14 yet another flowchart depicting a method for detection and characterization of one or more medical pathologies within an object under study according to one embodiment of the invention.

6. DETAILED DESCRIPTION OF THE INVENTION

The present invention is directed to a method and apparatus for generating real-time analyses of complex biological electrical parameters for the detection and characterization of medical pathologies. There are several aspects of the present invention, which are discussed in detail below.

6.1. Introduction

The present invention uses a computer controlled process of tissue discrimination that uses both static skin surface electrical potentials and complex impedance measurements. In the preferred embodiment of the invention, the input driving currents use a wide dynamic range and define nonlinear effects for frequency domains with marked noise rejection. In other embodiments, time domain analyses are performed, although the noise-rejection potential in such embodiments is less efficient than in the preferred embodiment. Characterization and localization are observed in phase delays, which are measured as functions of changing frequency and amplitude.

One aspect of the present invention is the coupling of electrical measurements of tissue with separate imaging procedures. By using electrical measurements to define accurately volumes of tissue that have low probabilities for cancer, premalignant characteristics, or other medical pathologies of interest, there is a marked reduction in the data analysis necessary for a complementary imaging analysis; such a complementary imaging requires less data analysis because it can focus on tissue regions that are identified by the impedance measurements to be of primary concern. Any appropriate complementary imaging technique may be used, including x-ray imaging, ultrasound imaging, mammography, CT imaging, MRI, SPECT imaging, and PET. The technical value of coupling the imaging technique with bioimpedance measurements is greatest when the imaging technique is computationally intensive. However, diagnostic value may be greatest when combining characteristic electrical information where interpretations are currently fraught by human error (i.e., mammography). Bioimpedance measurements are thus used to narrow the region to be studied with the complementary imaging technique so that the computational aspects of the complementary technique are used more productively. This is the case, for example, where a three-dimensional image is generated by the complementary technique instead of a two-dimensional image. In a preferred embodiment of the invention, the bioimpedance measurements are coupled with an ultrasound imaging technique or digital mammography.

6.2. Measurements

In general, the invention functions by affixing a plurality of electrodes to the subject's skin in a pattern around the region of interest. The electrodes act as sources and sinks of electrical current, so that a plurality of channels within the tissue of interest are electrically stimulated. The sensitivity and resolution that can be achieved are dependent on the number of electrodes that are used and, correspondingly, on the number of stimulation channels available for analysis. In one embodiment of the invention, the number of electrodes is as small as 3. In a preferred embodiment, useful where the human breast is studied for the presence of cancer, the number of electrodes is of the order of 10. In other embodiments, the number of electrodes is as large as $10^4$. A number of electrodes intermediate between these values is within the scope of the invention, as are still larger numbers of electrodes, depending on the type of tissue to be analyzed, the type of diagnosis that is to be made, and the sensitivity and resolution that are desired.

Rather than stimulating channels with a voltage waveform, as has been done in the prior art, the invention operates by stimulating the tissue using a current waveform. The current waveform preferably has an oscillation frequency between 2 Hz and 2 MHz. The magnitude of the current waveform is preferably between 10 nA and 1 mA. The precise current waveform profile is achieved by injecting electrons at the rate required by the profile at the sinks and extracting electrons at the required rate at the sources. In a preferred embodiment of the invention, this waveform profile is sinusoidal. Other embodiments of the invention include, without limitation, square, triangular, ramp, pulse, and sinc waveform profiles [where sin c $x \equiv (\sin x)/x$]. In a preferred embodiment of the invention, noise sources (which are not at the same frequency and at a constant phase angle from the drive sources) are eliminated by using digital-signal-processor-based lock-in amplifier.

The skin tends to have a significantly larger impedance than does the underlying tissue that is to be studied. Consequently, in prior-art approaches in which a precise potential gradient is imposed on the surface of the skin, variations in the large intrinsic impedance of the skin mask to some extent the underlying tissue impedance under study. By instead imposing a precise current profile to the skin, the imposed current rapidly diffuses through the skin and into the underlying tissue because that tissue has significantly less resistance to electrical flow. Any variation in the skin-potential mosaic, or in the skin impedance, is compensated by a compliance voltage adjustment of the current source, and does not systematically alter the intended measurement within the level of ideal performance of the current source synthesizers.

The data that are measured with each of the electrodes include the complex impedance Z (amplitude and phase), the derivative of the complex impedance with frequency $dZ/d\omega$ (amplitude and phase derivative), and information on the fluctuations of both quantities over time. These data are acquired as a function of frequency, current drive amplitude, and vector direction of the aggregate current relative to the electrode location on the tissue. These raw data are used to infer parameters within the bioimpedance continuum model described in detail below, as well as to detect departures from the expected value of these parameters that flag the early occurrence of a pathology. In general, a change in impedance magnitude and phase angle with frequency provide information on the relaxation time of the ionic currents and molecular polarizations of the ions along the path of the ionic current that is being excited. Such variations are indicative of the early formation of pathologies. In addition, these data are correlated with the drive amplitude to detect departures from linear response. Departures from linear response indicate when local potential variations at the cellular level become large enough to overcome cellular potential variations, and thus allow new ionic conduction paths to be taken. Such nonlinearities do not normally exist in healthy tissue with large cellular potentials. However, when depolarization occurs in and around cancerous tissue, then such nonlinearity occurs much more readily.

6.3. Continuum Model

Figure 1:
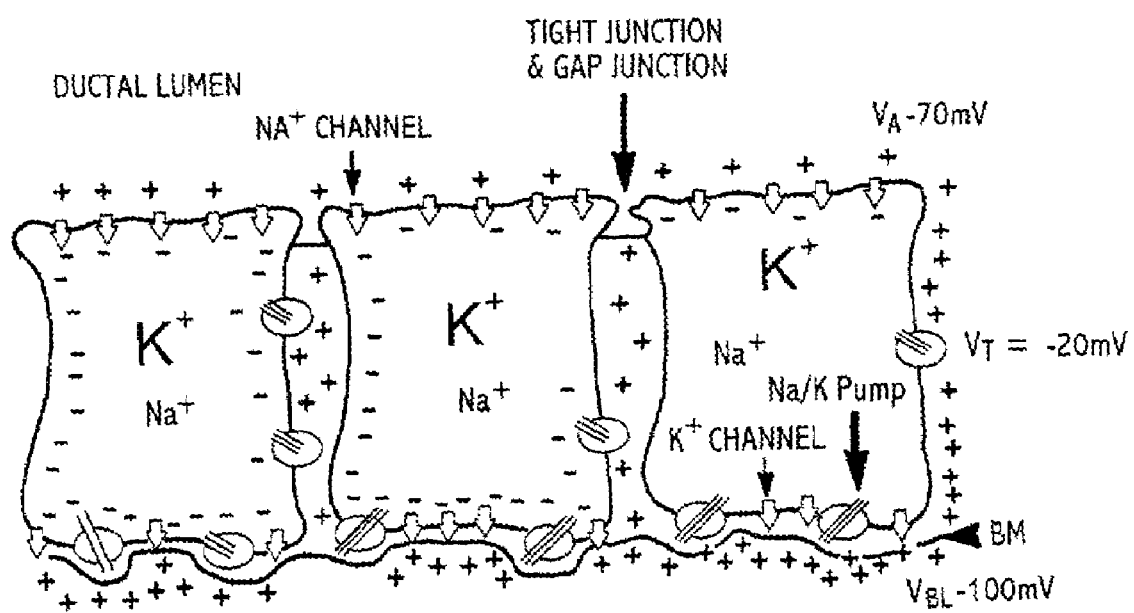

The development of an electrical model of the epithelium is most easily understood with reference to FIG. 1, which shows the electrical gradients that exist in epithelial tissue. A more straightforward visualization of the origin of the various model elements is possible with reference to FIG. 2(*a*), which illustrates the electrical structure of the epithelium more schematically. As shown in the figure, there is a positive charge external to each cell in the epithelium. In the lumped-element model used by Davies et al. [Biophys. J., 52, 783 (1987)], there is correspondingly a total extracellular resistance $R_e$ along the epithelium, a total intracellular-fluid resistance $R_i$, and a total cell-membrane capacitance $C_m$ created by the positively charged parallel membranes of the epithelial cells. In this simple model, using total values for each of the electrical parameters, the intracellular-fluid resistance $R_i$ is in parallel with the cell-membrane capacitance $C_m$, both of which are in series with the extracellular resistance $R_e$. This is evident from the physical layout of the epithelium shown in FIG. 2(*a*) and is shown in an electrical schematic in FIG. 2(*b*). This early model did not allow nonlinearities, nor did it model the inductive reactance of the tissue.

Such a simple lumped-element model clearly does not account for the true complexity of the system. First, there is no real justification for the assumption that the system can accurately be studied by using a single value for $R_e$, $R_i$, and $C_m$. The epithelium is, in fact, a continuum electrical system, which is more properly represented by an infinite series of electrical components. Such a system is illustrated for purely resistive elements in FIG. 2(*c*)(i), where each $r_e$ represents the extracellular resistance for an epithelial element $\varepsilon$. and each $r_i$ represents the intracellular-fluid resistance for the same epithelial element. As the number of electrical elements in the system $N \rightarrow \infty$, the size of the epithelial elements $\varepsilon \rightarrow 0$ and the epithelium is modeled as a continuum.

The use of purely resistive elements permits a simple analytic demonstration of how such a continuum electrical model may be solved. The total resistance R may be calculated by recognizing that, as a consequence of the infinite number of elements, that portion of the circuit to the right of any $r_i$ may be replaced by a resistance R; FIG. 2(*c*)(ii) is the simplest (of infinitely many) such equivalent circuits, and it may be solved by using standard techniques for combining resistances in series and in parallel:

$$R = r_e + \left(\frac{1}{r_i} + \frac{1}{R}\right)^{-1}$$

so that, solving for R, $$R = \frac{r_e + \sqrt{r_e^2 + 4 r_i r_e}}{2}.$$

In the particular instance where $r_i = r_e \equiv r$, $$R/r = \frac{1+\sqrt{5}}{2} = \varphi.$$

where $\Phi = 1.618\ldots$ is the so-called Golden Mean or Divine Proportion.

Another complexity of the system that is not accounted for in the prior-art lumped element models is the inclusion of inductive elements in the reactances of the model. Additionally, the prior-art models implicitly rely on the assumption that ionic transport through tissue is linear. However, the extent to which nonlinearity of such transport exists and can be identified is a farther parameter that may be used in diagnostic analyses of tissue. In particular, conductance nonlinearities serve as an excellent indicator of cell-membrane depolarization during the very early stages of cancer formation. The model of the present invention, the circuit diagram for which is illustrated in FIG. 2(d), is not only a continuum model, but also includes both inductive elements and circuit elements that model the nonlinearity of ionic transport.

Figure 2D:
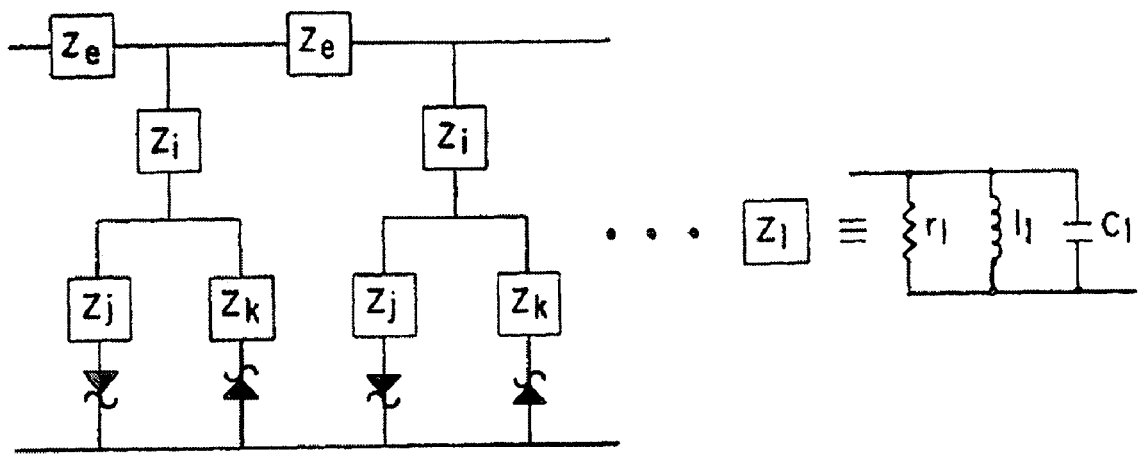

As shown in FIG. 2(d), each of the impedance elements in the circuit is defined so as to contain a resistive, capacitive, and inductive element. Further, the circuit contains Zener-diode elements that model nonlinearities in electrical conductance. As will be recognized by those of skill in the art, a Zener diode impedes the flow of current in a given direction, but has a predetermined breakdown voltage; this breakdown voltage is such that current will flow even in the opposed direction provided the potential difference across the Zener diode exceeds the breakdown voltage. In the circuit shown in FIG. 2(d), there are two Zener diode elements placed in parallel and in opposing directions. Current flow through one of the parallel branches is impeded unless the potential difference is sufficiently high; if the potential difference exceeds the breakdown voltage, then current will flow through both branches. This consequently introduces a nonlinearity into the electrical conductance that would not exist within the model without the Zener-diode elements. This reverse breakdown potential corresponds to the cell membrane polarization potential, appropriately modified by ionic screening and the counter-polarization of surrounding molecules. In a preferred embodiment of the invention, where the magnitude of the applied current waveform is between 10 nA and 1 mA, there are five orders of magnitude in current drive over which the nonlinearity in the conductance of the tissue may be studied.

The inductive elements in the model circuit account for uninterrupted current flow while the capacitive elements account for partial current interruption due to ions that cannot cross the epithelium. The capacitive signature displays the increase in epithelial impediment to ion flow through damaged epithelial cells, which results from the onset of macromolecular ionic flow across the epithelium once depolarization occurs. The healthy epithelium only readily permits light ions to pass through, resulting in a much easier ionic current through the cell, and hence a lower value of $R_i$ and a very low value of $C_m$. However, when the membrane depolarizes, it acquires macromolecular ions that give very little net ionic current transport for a given potential; this results in a higher value of $R_i$ and a much higher value for $C_m$. One reason the value of the reactive inductance is informative is because it responds to interruptions of ionic current. In one embodiment of the invention, the value of the inductance is used to infer alternation in the membrane protein expression of the connexin gene CX-43, which can occur during early stages of cancer. The reactive inductance is also strongly correlated with the $R_e$ signature when the epithelium is healthy, and is not strongly correlated when the epithelium has been damaged by cancer.

6.4. Display and Analysis of Data

After the various components of the impedances are measured, they are studied in both real time and space, and in fast-Fourier-transform space. As a result, dynamic fluctuations in these quantities are easily studied so that variations in dynamic response trends during cancer formation are readily detected. While the invention encompasses measurement and analysis of any set of capacitance, induction, and resistance values, preferred embodiments focus on the measurement and analysis of parameters that are most relevant to the specific pathology to be identified. For example, in one embodiment where the objective is to identify cancerous or precancerous tissue, the set of parameters $\chi \equiv \{\chi_i\} = \{c_m, r_i, r_e, l^m\}$ is determined from the measurements. These parameters represent, respectively, the differential cell-membrane capacitance, the intracellular-fluid differential resistance, the extracellular differential resistance, and the differential surface membrane inductance of the continuum model. In addition, from the use of the time-series data and the different spatial paths excited by the electrode geometry, the range of variation in each of these quantities $\delta\chi \equiv \{\delta\chi_i\} = \{\delta c_m, \delta r_i, \delta r_e, \delta l_m\}$ is measured. This information is correlated with the current amplitude $I_0$ and frequency $\omega$, which permits the observation of nonlinearities in the impedance to the extent they exist, and the characteristic ionic and polarization relaxation times.

Figure 3:
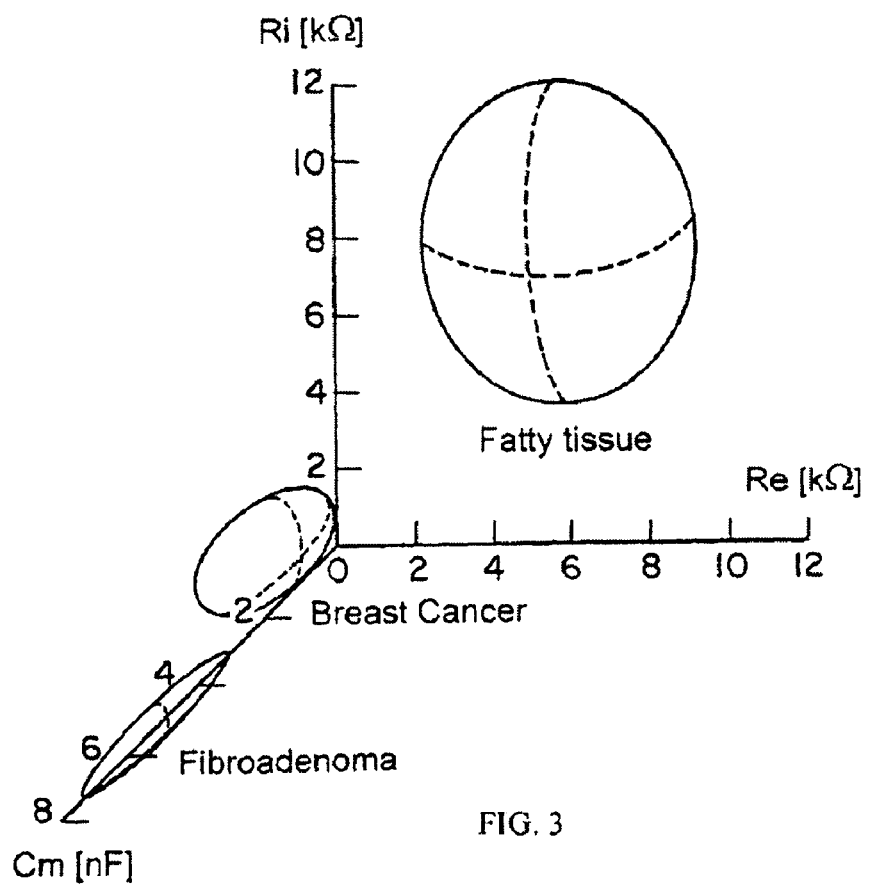

Thus, in this embodiment, the results of the bioimpedance measurements are organized in a ten-dimensional space. This is to be contrasted with prior-art techniques that have made use of much less sophisticated and much less extensive information. For example, in Morimoto et al., J. Invest. Surg., 6, 25 (1993), results of measurements defining the three parameters $R_i$, $R_e$, and $C_m$ for breast tissue were organized into a three-dimensional space based on these parameters, as illustrated in FIG. 3. Similar results were presented for lung tissue in tabular form. As can be seen from even a superficial examination of the figure, various types of tissue were assigned to specific regions in this three-dimensional space. Importantly, however, the region of FIG. 3 that corresponds to normal breast tissue was not shown explicitly in the figure in Morimoto. In fact, it overlaps almost completely the fibroadenoma region and has a strong overlap with the breast cancer region, making it impossible to use such a limited parameter space for accurate diagnoses. There exist two primary drivers: First, increased sensitivity is required to obtain noise levels that are intrinsic to the tissue and not the measurement instrument, and secondly the model must have adequate fidelity to provide specificity between tissue that is healthy and that which is pathological. Moreover, the analysis in Morimoto did not consider other tissue types that may be present, such as parenchyma, fatty parenchyma, parenchymal fat, and subcutaneous fat, and which may well also overlap regions of healthy tissue and different diseased tissue within the limited three-dimensional parameter space. Examples of strong overlap of different tissue types is also found in the tabular results for lung tissue. Consequently, the usefulness of the Morimoto method and results are diminished by its limitation to a three-dimensional space, and the over-simplified lumped-element model.

Davies et al., Biophys. J., 52, 783 (1987) went beyond this in an analysis of mouse gut epithelia in order to understand an impedance analysis of experimentally induced colon cancer.

In that instance, the three parameters used by Morimoto et al. were also correlated with the peak self-resonant frequency $\omega_0$ and its associated peak resistance $R_0$. Although this type of analysis is in principle better, it still does not permit nearly as complete an identification and diagnosis of tissue as does the current invention, which makes use of considerably more information that is directly relevant to such a diagnosis. Curiously, this work did not explicitly model the tissue's inductive reactance, however, the observed self-resonant frequency $\omega_0$ corresponds to the frequency when the tissue's aggregate inductive and capacitive reactances are equal in magnitude.

The utility and effectiveness of the information that makes up the ten-dimensional space of the present invention can be enhanced with various techniques. In different embodiments, the ten-dimensional space is reduced to a space with a smaller number of dimensions by contracting $\chi_i$ with $\delta\chi_i$ for one or more values of i. In a preferred embodiment the contraction is performed for all four values of i; specifically, $c_m$ is contracted with $\delta c_m$, $r_I$ is contracted with $\delta r_i$, $r_e$ is contracted with $\delta r_e$, and $l_m$ is contracted with $\delta l_m$. This results in a six-dimensional space in which regions corresponding to $\chi_i \pm \delta\chi_i$ are defined. In order to determine what type of tissue is represented by the measured values, the position of the point in ten-dimensional space is compared with a predetermined signature to evaluate the tissue type. Alternatively, in embodiments where the ten-dimensional space has been contracted, an n-dimensional volume in the contracted (10–n)-dimensional space is compared with a region in a predetermined sample. Specifically, in the embodiment where every $\chi_i$ is contracted with $\delta\chi_i$, the region occupied by the four-dimensional volume defining the results of the measurement within the six-dimensional space is compared with predetermined signatures for different tissue types. Supplemental data may also be obtained by performing a fast-Fourier transform on the time series $\delta\chi_i(\tau)$. Such a frequency-domain analysis may indicate unhealthy and intermittent impedance to blood and ionic flow resulting from a pathology.

Figure 4:
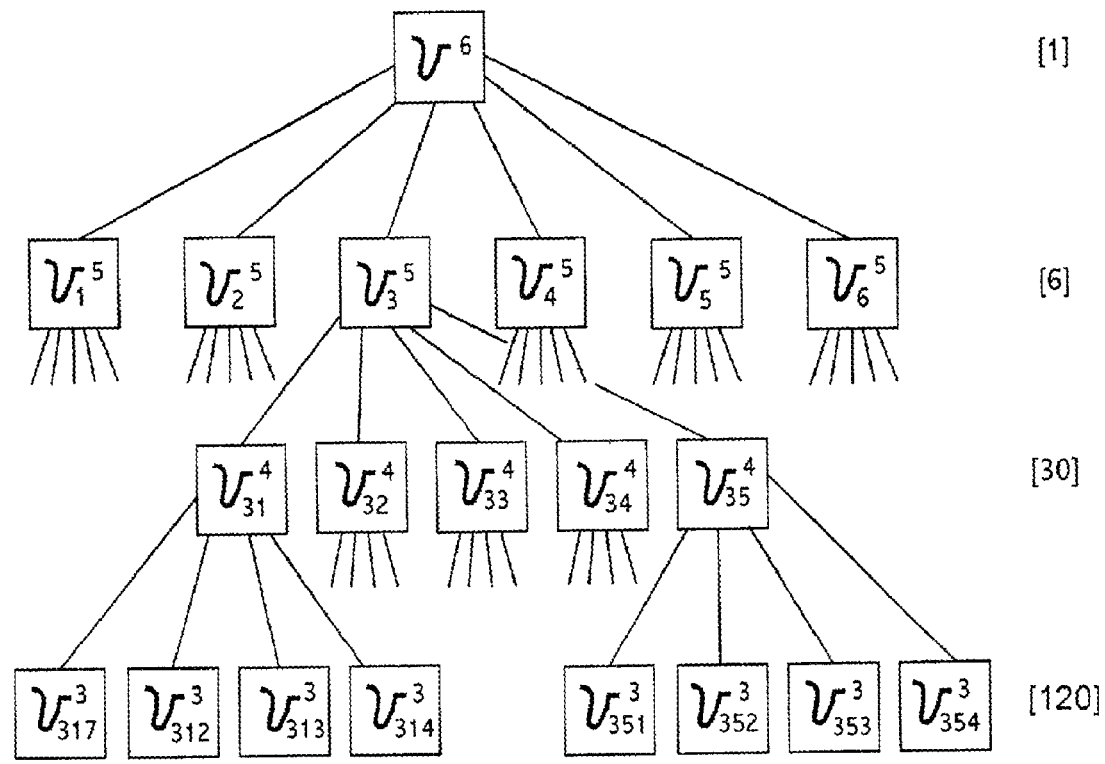
FIG. 4 illustrates the projection of a single six-dimensional space onto a series of 120 independent three-dimensional spaces.

It will readily be appreciated by those of skill in the art that as a result of the high dimensionality of the spaces involved, it is not possible for any unaided human being to do the comparison, as might be possible using the more primitive approach of Morimoto. Indeed, it is not possible for a human being even to visualize in any meaningful way the occupation of the four-dimensional region within the six-dimensional space. Accordingly, it is preferred that three-dimensional slices of the six-dimensional space by extracted computationally. This is accomplished by a series of projections onto progressively smaller spaces until the entire six-dimensional space has been extracted, as illustrated in FIG. 4. Specifically, the entire six-dimensional space, which will be denoted by $v^6$, is projected along six orthogonal directions into six five-dimensional spaces, $Pv^6 \to \{v^5{}_\alpha\}$. Each of the resulting five-dimensional spaces is further projected along five orthogonal axes into five four-dimensional spaces, $Pv^5{}_\alpha \to \{v^4{}_{\alpha\beta}\}$. Finally, each of the resulting four-dimensional spaces is projected along four orthogonal directions into four three-dimensional spaces, $Pv^4{}_{\alpha\beta} \to \{v^3{}_{\alpha\beta\gamma-}\}$. Since, in this notation $1 \leq \alpha \leq 6$, $1 \leq \beta \leq 5$, and $1 \leq \gamma \leq 4$, the result of the series of three projections $P^3 v^6 \to \{v^3{}_{\alpha\beta\gamma}\}$ is $6 \times 5 \times 4 = 120$ distinct three-dimensional space projections. As will be understood by those of skill in the art, the four-dimensional region defined by $\chi_i \pm \delta\chi_i$ will be mapped into one of a three-dimensional volume, a plane surface, or a point in the various three-dimensional projections, depending on the values of $\alpha$, $\beta$, and $\gamma$. It will further be appreciated by those of skill in the art that although the series of projections has been illustrated for the preferred embodiment in which the space is six-dimensional, a similar series of projections may be performed for any dimension of the space. For instance, in an embodiment where only two of $\chi_i$ are contracted with $\delta\chi_i$, the fivefold projection of the resulting eight-dimensional space, $P^5 v^8$, results in 6,720 three-dimensional spaces in which the two-dimensional region associated with the contracted $\chi$ appear as plane surfaces or points. The intent is to define what particular feature in this higher-dimensional space provides the greatest specificity. For the detection of very early cancer formation on the ephitelium, well before the pathology accesses the basic cell layers and metastecizes. If this feature is readily represented in one of these many possible three-dimensional projections of the full data set, then that feature will be displayed in the conventional manner. If not, then a more advanced algorithm will be used to detect the characteristic correlations in this high-dimensional space.

6.5. Development of a Diagnostic Signature Pattern

A trained evaluation system, such as an expert system or neural network, is employed to identify and learn the signature pattern of different tissue types within the multidimensional space, whether it be six-dimensional or otherwise. Once that is done, the trained evaluation system determines which of the three-dimensional projections is most clear for displaying the pattern of interest, and displays that single projection for viewing by an operator. Additionally, the trained evaluation system uses the information available in the multidimensional space for identification of abnormal conditions, including cancerous and precancerous tissues. Such a calculation is performed for every current path that is used, and the trained evaluation system follows the gradient in abnormality in its selection of future current paths, thereby localizing the abnormality.

In order for the trained evaluation system to identify the signature pattern of different tissue types, it uses a pattern-recognition algorithm, and identifies regions within the multidimensional space that correspond to the different tissue types. In any specific implementation of this pattern-recognition algorithm, it is necessary to ensure that the trained evaluation system is making reliable assignments. This is done by preliminary training of the evaluation system with an appropriate set of certifiable data that accounts for relevant risk factors, which is then encoded before the system is used to evaluate real data. For example, a number of sample results within different pattern groups may be provided to a set of physicians to assess the accuracy of the expert system's assignment against a physical examination of the tissue. The information extracted from the physicians' assessments is used to train the evaluation system's pattern-recognition algorithm.

This higher-dimensional space must be reduced to the most useful projection in order to permit accurate cancer diagnostics. In order to accomplish this reduction of the possible display variables, the subject invention will utilize an expert system that will actively re-direct the search based on detected anomalies, where anomalies are defined to be measurements which fall more than a given distance (typically two standard deviations) outside the norm for healthy tissue. This norm may be established statistically from the general patient population, or it may be established from the history of prior scans on a particular patient. Once the expert system detects an anomaly, it restricts and re-defines the search to more precisely quantify this anomaly. This may include the selection of particular current paths, and particular potential sense pairs, the selection of a specific measurement frequency ranges, the selection of a specific range of measurement currents, and the selection of a specific acoustic amplitude and frequency profile. In summary, all of these measurement parameters, including measurement current paths, potential sense pairs, frequency range of the applied current, amplitude range of the applied current, and frequency and amplitude range of the applied acoustic power will be dynamically assigned by the expert system as the expert system actively isolates the anomaly in this high-dimensional parameter space.

There are various ways of defining the regions in the multidimensional space that correspond to different tissue types as part of the training algorithm. The training algorithms to make this association include the use of expert systems; neural nets; stochastic optimization, wherein the shape of curves encompassing certain interpretations is changed by using methods such as steepest descent or simulated annealing; and evolutionary methods, wherein that shape is changed by a genetic algorithm. See generally, Stanley R. Deans, *The Radon Transform and Some of Its Applications* (Krieger Publishing, 1993), which is herein incorporated by reference. In general, such techniques fall into one of two classes. In the first class, the method begins with an initial approximation that is progressively improved. In the second class, the system is permitted to vary essentially randomly and individual constructions that develop during the process are evaluated to determine which best reproduces the observed data.

The use of a neural net that is trained to perform the identification accurately and consistently falls within the first class. See, for example, Simon S. Haykin, *Neural Networks—A Comprehensive Foundation*, pp. 352-434, 473-495 (Prentice Hall, 1998), which is herein incorporated by reference. A typical neural network includes a plurality of nodes, and each node has a weight value associated with it. One layer is an input layer having a plurality of input nodes, and another layer is an output layer having a plurality of output nodes, with at least one layer therebetween. In this embodiment of the invention, the input nodes receive the values of the complex impedance and the output node generates an interpretation designation of the tissue type. In other words, given an input comprising the complex impedance at one volume element of the multidimensional space, the input is combined (added, multiplied, subtracted in a variety of combinations and iterations depending upon how the neural network is initially organized), and then the interpretation is generated accordingly.

In order to train the neural net, the output values are compared against the correct interpretation with some known samples. If the output value is incorrect when compared against such a test interpretation, the neural net modifies itself to arrive at the correct output value. This is achieved by connecting or disconnecting certain nodes and/or adjusting the weight values of the nodes during the training through a plurality of iterations. Once the training is completed, the resulting layer/node configuration and corresponding weights represents a trained neural net. The trained neural net is then ready to receive unknown data and designate interpretations. Classical neural nets include Kohonen nets, feed-forward nets, and back-propagation nets. These different neural nets have different methods of adjusting the weights and organizing the respective neural net during the training process.

Several of the methods for training the evaluation system fall into the second class. One such method involves probabilistic estimation. The basic concept of probabilistic estimators is to designate discrete volume elements of the multidimensional space in terms of probabilities of certain tissue classifications given a certain input value. For instance, given a set of values for a particular multidimensional volume element, the probability that that volume element represents a particular interpretation is first determined. The volume element is then identified as the region with the highest probability. Test information is used to generate the basic probabilities. For example, in the embodiment where breast tissue is studied, there is a probability of certain types of tissue or tissue pathologies based on the calculated complex impedance values for the individual volume elements.

In more specialized stochastic estimation schemes, some regions of the multidimensional space are given more weight than others in order to reduce the rate of false positives or negatives. It will readily be understood that in different embodiments of the invention, it is more desirable to minimize either the rate of false positives or the rate of false negatives. For example, in the particular embodiment where cancer is to be identified in tissue, some level of false positives may be acceptable since a positive identification of cancer will be followed by additional medical procedures; however, it is desirable that the level of false negatives be minimized.

Another method that falls within the second class is a genetic algorithm, which is a model of machine learning that derives its behavior in an attempt to mimic evolution in nature. See, for example, Melanie Mitchell, *An Introduction to Genetic Algorithms*, pp. 35-78, 155-177 (Complex Adaptive Systems, 1996), which is herein incorporated by reference. This is done by generating a population of individuals represented by chromosomes, in essence a set of character strings that are analogous to the base-four chromosomes of DNA. The individuals in the population then go through a process of simulated "evolution." The genetic algorithm is widely used in multidimensional optimization problems in which the character string of the chromosome can be used to encode the values for the different parameters being optimized. In practice, therefore, an array of bits or characters to represent the chromosomes, in this case tissue types based on values of the complex impedance, is provided; then bit manipulation operations allow the implementation of crossover, mutation, and other operations.

When the genetic algorithm is implemented, it is trained in a manner that involves the following cycle: the fitness of all individuals in the population is first evaluated; then, a new population is created by performing operations such as crossover, fitness-proportionate reproduction, and mutation on the individuals whose fitness has just been measured; finally, the old population is discarded and iteration is performed with the new population. One iteration of this loop is referred to as a generation. In the present invention, a number of randomly generated tissue types are used as the initial input. This population of tissue types is then permitted to evolve as described above, with each individual tissue type being tested at each generation to see if it can adequately reproduce the observed data.

It will readily be understood by those of skill in the art that the most appropriate technique to use in training the evaluation system will depend greatly on the speed of the technique in light of the computational capacity of the hardware and software that is used to perform the computations. While the invention has been described in detail with specific examples of trained evaluation systems, the invention is not so limited and encompasses alternative schemes to do so.

6.6. Use of Compression Waves

In preferred embodiments of the invention, diagnosis of pathologies using bioimpedance measurements is coupled with the use of a compression wave. This method preferably uses acoustic waves generated from a plurality of acoustic sources placed on the skin near the tissue to be studied. The sound waves may then be focused to constructive interference at specific small volumes that have been identified within the tissue under study, provided that the acoustic wavelength is adequately short. The actions of such coherent ultrasound on the variation of the bioimpedance and its nonlinear response, as described in detail above, are measured and used to localize the presence of an impedance anomaly more precisely. At lower frequencies the acoustic wave creates a uniform pressure variation throughout the tissue under study. The change in the bioimpedance with and without insonificarbon at these low frequencies provides a signature of a pathology, as detailed below.

In addition to this information, the induced pressure wave caused by the ultrasound pulse produces compression of the tissue under study, which alters the complex-impedance characteristics of the tissue. Extensive work in elastrographic ultrasound imaging has demonstrated that the Young's modulus of tissue compressibility is significantly different for cancer than for benign tissue, thus highlighting different ultrasound impedances and imaging possibilities. Similarly, it is known that both temperature and pressure changes alter the electrical conductivity, and thus the complex impedance parameters, of tissue. Many proteins in connective tissue and muscle are piezoelectric or ferroelectric, meaning that they develop large electric fields under compression. Hence, insonification creates a local, deep electrical drive in phase with the acoustic wave. This deep electrical source in turry drives electrical currents that may be used to study variation in the impedance of nearby tissue. Hence, by measuring surface potential variations in-phase with the acoustic drive the bioimpedance of deep tissue may be inferred. Once again, the bioimpedance signatures with and without resonification may be measured, and the change will be indicative of some local, deep abnormality. Thus, the evaluation system is trained in some of these embodiments by providing complex-impedance data collected for the same tissue both when insonified and when uninsonified. In other embodiments, the evaluation system is trained with data collected for tissue within an insonified volume and adjacent tissue that is uninsonified. Combining the modulating effect of focused ultrasound upon the electrical signal is preferably used to characterize further any initial electrical signals that are particularly difficult to differentiate as benign, premalignant, or malignant.

6.7. Glove Sensor System

In a preferred embodiment of the invention, the electrodes are affixed to gloves with at least one driving electrode per finger pad. In this embodiment, the practitioner is thus able to move the electrode array in response to real-time three-dimensional images extracted by the trained evaluation system and in response to his own observations of a patient. This provides the capability for palpation assessment of tissues, intraoperative assessment of tissues, and general physical diagnosis. In one embodiment, the gloves additionally include a plurality of position sensors, which are used to provide position data that are overlaid with the complex-impedance data. In this manner, abnormalities that are detected are readily localized. A three-dimensional impedance image in real-time can be generated in this embodiment for a volume of tissue defined within the estimated enclosure of the fingertips or hands.

This embodiment also permits a compression modulation of the tissue electrical impedance without the use of ultrasound. The compression modulation is instead achieved by palpation. While this may be of particular importance for superficial tissues, it still permits elicting data from more central organs or tumors via deep palpation. Similarly, intraoperative direct compression of questionable tumors, or organs with possible tumor involvement, may show improved electrical signal characterization during direct compression. This does not preclude additional modulation by ultrasound even when the tissue is under palpable compression.

6.8. Coupling with Acoustic Data

In addition to impedance and potential measurements, the invention encompasses additional analog drive and digitization channels that are used to excite and sense small acoustic signals in the body. Such measurements are used in sensor fusion with the bioimpedance data, permitting much more specificity in the detection of disorders associated with pathologies other than cancer alone. This approach provides a class of measurements that are indicative of the effects of the pathology on the overall biological system.

There are three distinct modes in which the acoustic subsystem of the invention is used. In each of these embodiments, an array of sensitive microphones is placed on the body at positions that a clinician considers to be most appropriate for the disorder under study. In a first embodiment, these microphones measure acoustic variations associated with the process under study, such as the heartbeat, blood flow through arteries and veins, respiration, neuromuscular activity, and the gastrointestinal tract. These passive acoustic data are preferably digitized at a rate of at least 30 kHz, and even higher rates are preferred if warranted by specific high-frequency abnormalities. The fast Fourier transform of the digitized acoustic data is calculated and compared with the resulting power spectra to that of healthy functional tissue. These data provide detailed functional data about heart health, and about air and fluid transport in organs that may become afflicted by any pathology. For example, many epithelial conditions create constrictions in the gastrointestinal tract, throat, lymphatic system, or circulatory systems that affect the flow of air and fluids and shift the resulting acoustic power spectrum to higher frequencies from their normal state. Typically such pathologies also create an intermittence which results in a greater spread in frequencies about a frequency that is indicative of a particular body process. This resulting spectral width in the Fast Fourier Transform (FFT) may provide an additional diagnostic tool.

In a second embodiment, a monochromatic acoustic wave at a preset frequency is excited by a loud speaker in contact with the body at a position determined by the clinician. The array of microphones detects only that part of the total acoustic response that is at the drive frequency, and at a constant phase relationship to the drive. The resulting magnitude of the sound observed at each microphone using this synchronous detection technique is used to infer the acoustic impedance magnitude and phase angle at that position in the array. This acoustic impedance is modulated by a slower (much slower compared to the period of the acoustic wave) biological process, such as the heartbeat, respiration, gastrointestinal activity, etc. These measurements provide far more detailed information and detect far more pervasive patterns specific to the pathology than do simple potential sensing, as in systems such as electrocardiography (EKG), electroencephalography (EEG), electromyography (EMG), etc. The technique may be used to detect changes by taking repeated measurements on an individual patient at different times. It may alternatively be used as an absolute screening tool to detect patients that fall well away from the mean of the general population.

In a third embodiment, the microphone array is taken out of the synchronous detection mode, and set to sense frequencies that are detuned from the drive frequency. This detection technique provides information about the nonlinear acoustic character of the tissue as a function of drive amplitude, and also as a direct sensor of acoustic Doppler-effect detuning associated with fluid flow or mass motion in the body.

6.9. Exemplary Applications

While the invention has been described above with particular reference to the detection and characterization of cancer within a human or animal body, it is not so limited. Several examples of the application of the invention to both oncologic and other applications are described below.

6.9.1. Oncologic

In several embodiments, the invention is used in the diagnosis of oncologic disease. While devices in the prior art are able to distinguish benign from proliferative (i.e. premalignant and malignant) epithelium, the more sensitive analysis of the invention permits reliable differentiation of premalignant and malignant conditions as well.

6.9.1.1. Multiple Techniques

In preferred embodiments, the invention is used in conjunction with at least one other diagnostic technique to improve the reliability and/or efficiency of the diagnosis. In one such embodiment, the complex bioimpedance analysis of the invention is used to exclude data analysis for a subsequent imaging technique that would otherwise be required. For example, if the subsequent imaging technique is ultrasound, the invention is used to identify regions within the volume under study that contain healthy tissue. The subsequent ultrasound measurements are then focused more particularly on the regions of the volume under study that have not been excluded. In an ultrasound technique that uses a large number of ultrasound detector elements, such as that described in U.S. patent application Ser. No. 09/272,452, which is herein incorporated by reference, the result is that there is a significant reduction in both the computational and detector requirements. Consequently, the ultrasound procedure is used more efficiently and its resolution is enhanced because the limited number of detectors are focused most particularly on a region identified as suspicious.

In other embodiments, the complex bioimpedance measurements are used subsequent to another technique that has been used to exclude data. In yet further embodiments, a plurality of techniques are used before, after, or in some combination of before and after, in conjunction with the complex bioimpedance measurements. In such embodiments, it is preferred that each of the techniques exploit its most efficient characteristic so that the combination of techniques includes the benefit of all the techniques used.

6.9.1.2. Assessment of the Efficacy of Cancer-Prevention Treatment

In another embodiment, the improved differentiation in the spectrum of disease progression towards cancer is exploited. In this embodiment, multiple measurements taken at different points in time on a single subject are evaluated to detect a reversion of some tissue from a suspicious, but not cancerous, state to a normal state. Such measurements are taken before and during medical, pharmacological or surgical intervention, and the efficacy of the intervention is studied statistically when applied to a suitably large number of subjects.

The invention is thus used in this embodiment for noninvasive testing of the response to any of a large number of therapies. The use of a reliable noninvasive efficacy evaluation results in marked cost savings for large trials when compared with invasive techniques and in greater reliability than is possible with other noninvasive efficacy-evaluation techniques. Additionally, the fact that the therapy is evaluated noninvasively results in an increase in both patient accrual and patient compliance.

Figure 5:
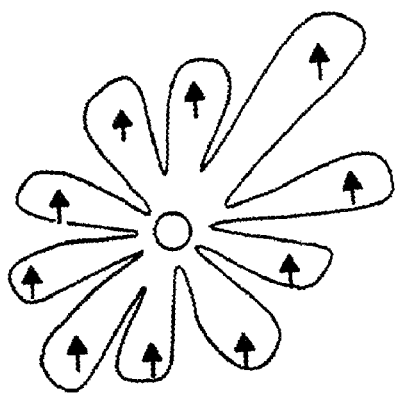
FIG. 5 illustrates the "flower petal" shape of an adhesive pad that maintains a fixed electrode configuration so that consistent measurements are obtained from different patients. The positions of the electrodes are indicated by arrows.

In a preferred embodiment, the arrangement of current sources and sensing electrodes is fixed for all participants in the therapy trial. In one embodiment, individual electrodes are positioned in equivalent positions on each of the participants. In a preferred embodiment, the electrodes are fixed on an adhesive pad, thereby ensuring uniform distances between each combination of source and sink among all of the participants. Such uniformity produces improved consistency in signal localization. An exemplary embodiment using a "flower petal" design for the adhesive pad is illustrated in FIG. 5. In this figure, the locations of the electrodes are represented by arrows.

6.9.1.3. Screening for Abnormal Proliferative Tissue

In yet another embodiment of the invention, bioimpedance measurements are used to screen for abnormal proliferative tissue. In this embodiment, regions of tissue under study are particularly characterized for biopsy confirmation of a diagnosis. Localization of the target region is performed with combined standard imaging guidance and electrical sensing. If an underlying mass is detected with a technique such as ultrasound in an electrically suspicious region, it is then easily targeted with a standard technique. Conversely, ultrasound may provide only an estimation of a parenchymal area in question that is then further assessed by needle measurements of electrical abnormalities in conjunction with skin surface electrodes during biopsy.

6.9.1.4. General Pathology

While the invention has generally been described for use with living human beings or animals, there is no such limitation, and in other embodiments the invention is used for general pathology and laboratory analyses. In such an embodiment, a fixed-element device uses electrodes within the walls of a container and measurements are derived from the central volume. This embodiment is useful for rapid analysis of cell cultures, surgical tissue specimens, small laboratory animals, and simulation models, which can be placed within the container.

Figure 6A:
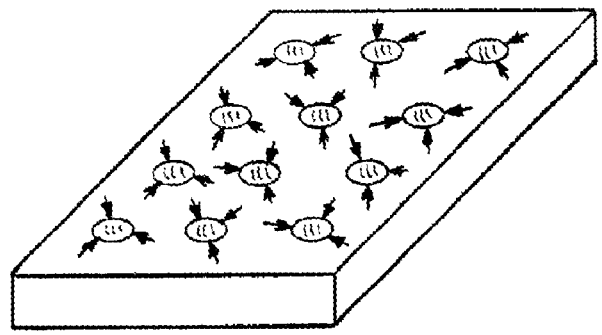
Figure 6B:
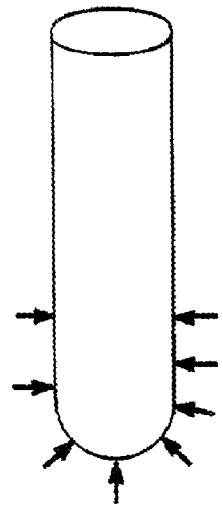
Figure 6C:
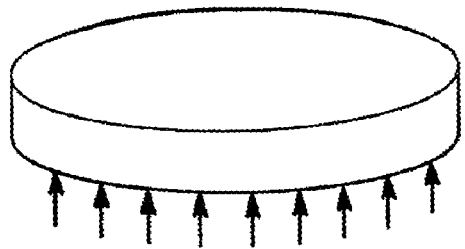

There are several such embodiments in which a fixed-element device is employed. Several of these embodiments are preferably used for the analysis of cell cultures. In one embodiment, illustrated in FIG. 6(a), a plurality of culture wells are arranged on a culture plate, with current sources and sensing electrodes disposed within the walls of the culture wells. In FIG. 6(a), and in all other subparts of FIG. 6 the positions of the electrodes are shown with arrows. In an separate embodiment, illustrated in FIG. 6(b), the current sources and sensing electrodes are disposed within the walls of a test tube. Preferably, the sources and electrodes are arranged in the lower part of the test tube where the sample naturally rests. In another embodiment, illustrated in FIG. 6(c), the container in which the walls contain current sources and electrodes is a Petri dish, which provides for a larger surface-area cell culture. Preferably, the sources and electrodes are distributed within the bottom plate of the Petri dish in a uniform distribution.

Figure 6D:
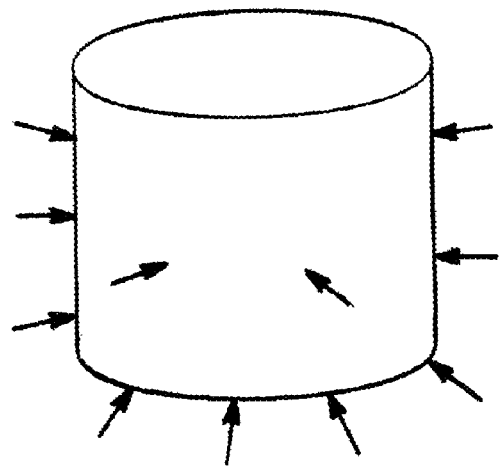

In a preferred embodiment, illustrated in FIG. 6(d) and useful for the analysis of tissue specimens, the container is a jar with a hemispherical bottom lined with sources and electrodes in its walls. The sources and electrodes are preferably evenly distributed. The container is used by placing a resected specimen within the container, which is preferably filled with a conductive fluid. The specific gravity of the fluid is preferably greater than for the tissue sample to be analyzed; for most applications, a specific gravity greater than 1.2 is sufficient. This causes the specimen to sink to the bottom of the container, thus limiting floating movement and resulting in better signal localization. In one embodiment of the invention, the results of bioimpedance measurements taken from a surgical specimen are compared with preoperative bioimpedance measurements taken with an array of current sources and electrodes appropriately placed on the subject prior to surgery. From such a comparison, a correlation is drawn between preoperative and postoperative bioimpedance measurements.

The invention is not limited to the containers described in detail above for particular embodiments, and those of skill in the art will readily recognize other containers that are within the scope of the invention. Furthermore, in alternative embodiments, the container is not lined with sources and electrodes; in such embodiments, bioimpedance measurements are taken from the object in the container with a needle that is inserted into the container. In these embodiments, the needle comprises current sources and electrodes, which are used to collect the bioimpedance data.

The invention also encompasses the use of bioimpedance analysis of laboratory animals in different embodiments. Small laboratory animals are analyzed by placing them in a container lined with current sources and sensing electrodes. Alternatively, an embodiment in which direct contact is made with the animal comprises a contact instrument lined on one surface with sources and electrodes. This embodiment may also be used to study human tissues when fixed placement of the sensing electrodes within the contact instrument is appropriate.

Use of the invention with living subjects is also coupled with pathology applications in other embodiments. For example, the localization of tissue abnormalities assists in subsequent pathologic sectioning and sampling. Similarly, tumor growth rates and treatment responses are rapidly monitored for in vitro specimens and are noninvasively monitored in experimental animal models.

6.9.1.5. Tissue Types

The invention concerns the detection of abnormalities in a number of different types of tissues and organs. While the description above has emphasized detection in the human breast, in which electrodes are placed on the breast to be studied, applications to other types of tissue are also within the scope of the invention.

In one embodiment, the invention is used to differentiate cancerous, precancerous, and benign tissue in the human prostate. In this embodiment, a plurality of electrical sources are placed over the lower anterior abdomen of the patient and the electrodes are placed in a probe within the rectal cavity. Other embodiments will also readily be recognized from the foregoing explanation that adapt various of the previously described applications to measurements of prostate tissue. Such applications include, without limitation, the use of position sensors on gloves equipped with electrodes, modulation of electrical impedance characteristics by compression waves or by palpation, and the coupling of various conventional techniques used in conjunction with bioimpedance measurements.

In another embodiment, the invention is used to differentiate cancerous, precancerous, and benign lymphatic tissue. In such an embodiment, a plurality of sources are placed over a lymph region, such as the neck, axilla, groin, or abdomen, with appropriately placed sensor electrodes within the same configuration. Other embodiments that adapt various of the previously described applications to lymphatic-tissue measurements, including the use of position sensors on gloves equipped with electrodes, modulation of electrical impedance characteristics by compression waves or by palpation, and the coupling of various conventional techniques, are also within the scope of the invention.

6.9.2. Applications to Non-Proliferative and Non-Cancerous Pathologies of Various Systems 6.9.2.1. Cardiac In other embodiments, the measurement of the complex electrical impedance results in improvements in electrocardiography. In the following, a standard electrocardiograph is referred to as an "EKG" and an electrocardiograph according to the present invention that makes use of complex impedance data is referred to as an "IKG." In all of the embodiments described in this section, the training of the algorithm used by the device is augmented by coupling the complex impedance measurements with standard EKG measurements so that features of a standard EKG known to be indicative of a pathology are used to identify more specific pathology characteristics in the IKG. Once the device is trained, it is used without the parallel EKG capability.

6.9.2.1.1. EKG/IKG

In one embodiment, both standard EKG measurements and the more sophisticated IKG measurements are taken from a single device. The device is equipped with electrodes that are used as both current sources and sinks, and contains programming that permits either analysis. The device is converted from EKG analysis to IKG analysis by a single switch. Because of the extensive analysis of nonlinear effects and the use of both inductive and capacitive data that are achieved with the IKG, it generally provides a much more specific signature of electrical abnormalities than the standard EKG. A device that permits both analyses is useful for two reasons, however. First, it is useful for training physicians in understanding the IKG results since they may determine a normal EKG and assign similar normal parameters to the IKG. Second, in clinical use where a cardiac pathology has been identified, a comparison of the EKG and IKG results can be used to elicit pathologic electrical parameters that are well defined in the IKG of the present invention but not in the standard EKG.

6.9.2.1.2. Electronic Stethoscope

In another embodiment, the EKG/IKG device is complemented with a plurality of microphones that are placed in adjacent positions to the electrodes to detect audible cardiac sounds. These microphones are attached to disposable horns that are shaped to focus the sound. The simultaneous and complementary detection of cardiac sounds with IKG measurements permits the identification of electrical abnormalities that are associated with valvular dysfunction. A training phase of neural networks permits physician input to the designation of abnormal cardiac sounds and possible associated electrical signals.

6.9.2.1.3. Electrophonic Stethoscope

In yet a further embodiment, the electronic stethoscope further comprises a modulation of electrical parameters by using chirped acoustic input. In this embodiment, the acoustic input signal is modulated through the available band of frequencies repeated at a fixed rate. Use of such a modulation enhances the desired signal while discriminating against unwanted signals, particularly by minimizing the effects of multipath echoes, noise crosstalk, and frequency shifts. Accommodated fusion merges this additional acoustic impedance information with the passive audible sound and electrical data sets.

6.9.2.2. Vascular

Embodiments of the invention use techniques that result in an understanding of vascular flow in the body. In a preferred embodiment, a microphone array is set asynchronously so as to sense frequencies that are detuned from the drive frequency. As explained above, this results in information about the nonlinear acoustic character of the tissue being collected as a function of drive amplitude. It also results in the detection of acoustic Doppler-effect detuning associated with fluid flow in the body. These results together provide detailed information on the velocity of blood flow in veins and arteries, including any possible occlusion or obstruction of the blood vessels.

In another embodiment, a concentrated magnetic field is imposed at a specific location in the body, and the resulting fluctuation in acoustic impedance and frequency detuning is recorded using both electric and acoustic channels. This information is indicative of the interconnectivity of blood flow through the tissue subjected to the magnetic field, thereby giving a detailed map of the interconnectivity and size of the interconnected blood vessels within the field. In specific embodiments, the magnetic field is scanned across the body, providing a spatially well-resolved map of the local circulation. The fluctuations, as evidenced by the width of the spectral lines using FFT, are very important indicators of pathology.

For both of these features, bioelectric impedance data is used in sensor fusion with the acoustic measurements. Because of the information that is collected describing blood flow, these embodiments are useful for the detection of the initial process of angiogenesis.

6.9.2.3. Pulmonary

In further embodiments, the electronic stethoscope and the electrophonic stethoscope are used to detect pulmonary pathologies in the same manner described for the detection of cardiac pathologies. Combining information obtained from both bioelectrical impedance measurements and acoustic impedance permits the identification of bronchus spasm, pneumothorax, hyperinflation, pulmonary edema, consolidation and potential neoplastic involvement.

6.9.2.4. Neurological

6.9.2.4.1. Brain Pathologies

In other embodiments, the standard electroencephalograph ("EEG") is modified to use the complex bioimpedance measurements of the invention in a manner analogous to that for modifying the standard EKG. Specifically, the use of very sensitive microphones with acoustic impedance data, coupled with complementary bioimpedance measurements, results in the collection of more data that can be correlated with pathologies associated with, for example, deep stenotic vessels within the brain to train the evaluation system. Once the evaluation system is trained, the device uses the evaluation system to detect pathologies by correlating the bioelectrical and acoustic measurements with specific pathologies.

These embodiments include an electroencephalograph that relies on complex impedance data rather than simply real impedance data ("EIEG") and an electrophonic encephaloscope, in which chirped acoustic input is used to provide a further modulation of the electrical parameters.

6.9.2.4.2. Neuromuscular Pathologies

In additional embodiments, similar modifications are introduced to EMG. In one embodiment ("EIMG"), complex bioimpedance data are collected to assess muscles of the torso and limb for their appropriate neurological response to interview stimulation. In one such embodiment, an electronic myograph uses bioimpedance data in conjunction with acoustic data. In another embodiment, an electrophonic myograph uses chirped acoustic data to provide a further modulation of the electrical parameters. These techniques may be used to provide specific and sensitive assessments of neuromuscular dysfunctions.

6.9.2.5. Skeletal

The use of sophisticated analyses of both complex electrical and acoustic impedance data are used in separate embodiments to highlight the existence of a bone fracture. In these embodiments, fracture is detected by characteristic signatures of nonlinear responses along the expected course of bones within a defined region. Both electrical and acoustic sources and detectors are placed appropriately around the expected trauma site. In this manner, marked cost reductions in trauma x-ray screening can be achieved.

The above examples are representative of the types of application to which the invention may be put, but the invention is not limited to the applications described. In particular, study of the examples will cause other applications to occur to those of skill in the art, and the invention encompasses all such applications as well.

What is claimed is:

1. An apparatus for detection and characterization of one or more medical pathologies within an object under study comprising:
    (a) a current source adapted to provide current with a predetermined current waveform, said current source being disposed so as to be capable of electrically stimulating such object;
    (b) a plurality of electrodes being disposed relative to such object to receive current from such object, each of said plurality of electrodes being capable of measuring a voltage;
    (c) means for controlling such current source and said plurality of electrodes to produce and receive current; and
    (d) a device coupled with said plurality of electrodes and configured to perform the steps of:
        (i) calculating a plurality of complex impedances, each of said plurality of complex impedances corresponding to a current drive path defined by said current source and one of said plurality of electrodes;
        (ii) constructing a multidimensional representation of the electrical characteristics of a region within said object under study using said plurality of complex impedances by solving a continuum electrical model that incorporates nonlinearities; and
        (iii) detecting and characterizing such one or more medical pathologies within said object under study from said multidimensional representation.

2. The apparatus according to claim 1 wherein said current source comprises a plurality of current sources.

3. The apparatus according to claim 1 wherein said plurality of electrodes includes at least one device that is used both as a current source and as a current sink.

4. The apparatus according to claim 1 wherein said plurality of electrodes comprises a re-configurable number of electrodes.

5. The apparatus according to claim 1 wherein said plurality of electrodes comprises three electrodes.

6. The apparatus according to claim 5 wherein said plurality of electrodes are disposed on a glove, a flexible membrane to attach to skin anywhere.

7. The apparatus according to claim 1 wherein said plurality of electrodes comprises more than 104 electrodes.

8. The apparatus according to claim 1 wherein said predetermined current waveform is harmonic.

9. The apparatus according to claim 1 wherein said predetermined current waveform has a profile selected from the group consisting of square, triangular, ramp, pulse, and sinc.

10. The apparatus according to claim 1 wherein said predetermined current waveform is periodic and comprises an oscillation frequency between 2 Hz and 2 MHz.

11. The apparatus according to claim 1 wherein said predetermined current waveform is periodic and has a magnitude between 10 nA and 1 mA.

12. The apparatus according to claim 1 further comprising means for reducing electrical noise.

13. The apparatus according to claim 12 wherein said means for reducing comprises a lock-in amplifier.

14. The apparatus according to claim 1 wherein said device further performs the step of calculating a plurality of complex impedance derivatives with respect to frequency, each of said plurality of complex impedance derivatives corresponding to a current drive path defined by said current source and one of said plurality of electrodes.

15. The apparatus according to claim 1 wherein said continuum electrical model comprises Zener-diode elements.

16. The apparatus according to claim 1 wherein said continuum electrical model comprises an inductive element.

17. The apparatus according to claim 1 wherein said continuum electrical model comprises:
(a) an inductive element;
(b) a capacitive element;
(c) a resistive element; and
(d) Zener-diode elements.

18. The apparatus according to claim 1 wherein said multidimensional representation is a ten-dimensional representation, or any reduced-dimensional representation.

19. The apparatus according to claim 18 wherein such object under study comprises human or animal tissue and said multi-dimensional representation comprises dimensions corresponding to differential cell-membrane capacitance, intracellular-fluid differential resistance, extracellular differential resistance, differential surface membrane inductance, range in variation of said differential cell-membrane capacitance, range in variation of said intracellular-fluid differential resistance, range in variation of said extracellular differential resistance, range in variation of said differential surface membrane inductance, amplitude of said current source, and frequency of said current waveform.

20. The apparatus according to claim 1 wherein said multidimensional representation is a six-dimensional representation.

21. The apparatus according to claim 20 wherein such object under study comprises human or animal tissue and said six-dimensional representation comprises dimensions corresponding to differential cell-membrane capacitance contracted with a range in variation of said differential cell-membrane capacitance, intracellular-fluid differential resistance contracted with a range in variation of said intracellular-fluid differential resistance, extracellular differential resistance contracted with a range in variation of said extracellular differential resistance, differential surface membrane inductance contracted with a range in variation of said differential surface membrane inductance, amplitude of said current source, and frequency of said current waveform.

22. The apparatus according to claim 1 wherein said device further performs the step of projecting said multidimensional representation into a plurality of low-dimensional spaces.

23. The apparatus according to claim 22 wherein said device further performs the steps of selecting one of said plurality of lower-dimensional spaces and displaying the selected lower-dimensional space.

24. The apparatus according to claim 1 wherein said device uses a trained evaluation system to perform said step of detecting and characterizing.

25. The apparatus according to claim 24 wherein said trained evaluation system comprises an expert system.

26. The apparatus according to claim 24 wherein said trained evaluation system comprises a neural net.

27. The apparatus according to claim 24 wherein said trained evaluation system uses stochastic optimization.

28. The apparatus according to claim 24 wherein said trained evaluation system uses a genetic algorithm.

29. The apparatus according to claim 1 wherein said object under study comprises a plurality of animal or human tissues.

30. The apparatus according to claim 29 wherein said plurality of animal or human tissues comprises a human breast.

31. The apparatus according to claim 29 wherein said plurality of animal or human tissues comprises a human prostate.

32. The apparatus according to claim 29 wherein said plurality of animal or human tissues comprises a human kidney.

33. The apparatus according to claim 29 wherein said plurality of animal or human tissues comprises a human lung.

34. The apparatus according to claim 29 wherein said plurality of animal or human tissues comprises a section of a human alimentary canal.

35. The apparatus according to claim 29 wherein said plurality of animal or human tissues comprises a human liver, heart or brain.

36. The apparatus according to claim 29 wherein said plurality of animal or human tissues comprises lymphatic tissue.

37. The apparatus according to claim 1 further comprising means for generating a compression wave within said object under study.

38. The apparatus according to claim 37 wherein said means for generating comprises an ultrasound source.

39. The apparatus according to claim 37 wherein said means for generating comprises a glove, whereby a practitioner generates said compression wave by palpation.

40. The apparatus according to claim 1 wherein at least one of said plurality of electrodes is disposed on a glove, a flexible membrane to attach to skin anywhere, or said ring of electrodes on elastic bands.

41. The apparatus according to claim 40 further comprising a position sensor disposed on said glove.

42. The apparatus according to claim 1 further comprising:
(a) a radiation source adapted to emit radiation within a predetermined frequency range or at a predetermined frequency onto a volume within such object under study, said radiation source being disposed so as to be capable of radiating such object; and
(b) a radiation detector disposed relative to such object to receive radiation scattered by said volume, said radiation detector being capable of providing data corresponding to the radiation received; and
wherein said device further performs the step of using said data in combination with said plurality of complex impedances to further characterize said one or more medical pathologies within said volume.

43. The apparatus according to claim 42 wherein said radiation source is a sound source and said radiation detector is a sound detector.

44. The apparatus according to claim 43 wherein said radiation source and said sound detector are fabricated in a single unit.

45. The apparatus according to claim 43 wherein said data are digitized.

46. The apparatus according to claim 45 wherein said data are digitized at a rate greater than or equal to 30 kHz.

47. The apparatus according to claim 43 wherein said sound source emits monochromatic radiation and said sound detector detects only scattered radiation that is at a constant predetermined phase relationship with said monochromatic radiation.

48. The apparatus according to claim 43 wherein said ultrasound source emits monochromatic radiation and said sound detector detects only scattered radiation that is detuned from said monochromatic radiation.

49. The apparatus according to claim 43 wherein said sound source emits chirped radiation.

50. The apparatus according to claim 43 wherein said one or more medical pathologies comprises a cardiac pathology.

51. The apparatus according to claim 50 wherein said cardiac pathology is a valvular dysfunction.

52. The apparatus according to claim 50 further comprising a standard electrocardiograph.

53. The apparatus according to claim 43 wherein said one or more medical pathologies comprises a vascular pathology.

54. The apparatus according to claim 53 further comprising means for imposing a concentrated magnetic field within said object under study.

55. The apparatus according to claim 54 further comprising means for scanning said concentrated magnetic field across said object under study.

56. The apparatus according to claim 43 wherein said one or more medical pathologies comprises a pulmonary pathology.

57. The apparatus according to claim 56 wherein said pulmonary pathology is selected from the group consisting of a bronchus spasm, pneumothorax, hyperinflation, eduma, consolidation, and a neoplasm.

58. The apparatus according to claim 43 wherein said one or more medical pathologies comprises a neurological pathology.

59. The apparatus according to claim 58 further comprising a standard electroencephalograph.

60. The apparatus according to claim 43 wherein said one or more medical pathologies comprises a neuromuscular pathology.

61. The apparatus according to claim 60 further comprising a standard electromyograph.

62. The apparatus according to claim 43 wherein said one or more medical pathologies comprises a bone fracture.

63. The apparatus according to claim 1 further comprising a container for holding said object under study wherein said current source and said plurality of electrodes are disposed within walls of said container.

64. The apparatus according to claim 63 wherein said object under study is a cell culture.

65. The apparatus according to claim 63 wherein said object under study is a surgical tissue specimen.

66. The apparatus according to claim 63 wherein said object under study is a laboratory animal.

67. The apparatus according to claim 63 wherein said object under study is a tissue equivalent model.

68. The apparatus according to claim 63 wherein said container comprises a plurality of wells in a plate.

69. The apparatus according to claim 63 wherein said container is a test tube.

70. The apparatus according to claim 63 wherein said container is a Petri dish.

71. The apparatus according to claim 63 wherein said container comprises a hemispherically shaped bottom.

72. The apparatus according to claim 63 further comprising an electrically conductive fluid within said container.

73. The apparatus according to claim 72 wherein said electrically conductive fluid has a specific gravity greater than said object under study.

74. The apparatus according to claim 72 wherein said electrically conductive fluid has a specific gravity greater than or equal to 1.2.

75. The apparatus according to claim 1 further comprising a contact instrument wherein said current source and said plurality of electrodes are disposed on one surface of said contact instrument.

76. The apparatus according to claim 1 further comprising a needle wherein said current source and said plurality of electrodes are disposed in said needle.

77. The apparatus according to claim 76 further comprising a container for holding said object under study.

78. The apparatus according to claim 77 wherein said object under study is selected from the group consisting of a cell culture, a surgical tissue specimen, a laboratory animal, and a tissue equivalent model or simulator and said container is selected from the group consisting of a culture well, a test tube, a Petri dish, and a jar with a hemispherical bottom.

79. An apparatus for detection and characterization of one or more medical pathologies within an object under study comprising:
(a) a current source adapted to provide current with a predetermined current waveform, said current source being disposed so as to be capable of electrically stimulating such object;
(b) a plurality of electrodes being disposed relative to such object to receive current from such object, each of said plurality of electrodes being capable of measuring a voltage;
(c) means for controlling such current source and said plurality of electrodes to produce and receive current; and
(d) a device coupled to said plurality of electrodes and configured to analyze data received from said plurality of electrodes to detect and characterize such one or more medical pathologies, wherein said device calculates a plurality of complex impedances, each of said plurality of complex impedances corresponding to a current drive path defined by said current source and one of said plurality of electrodes, and constructs a multidimensional representation of the electrical characteristics of a region within said object under study using the plurality of complex impedances by solving a continuum electrical model that incorporates nonlinearities.

80. The apparatus according to claim 79 wherein said predetermined current waveform is sinusoidal.

81. The apparatus according to claim 79 wherein said predetermined current waveform has a profile selected from the group consisting of square, triangular, ramp, pulse, and sinc.

82. The apparatus according to claim 79 wherein said predetermined current waveform is periodic and comprises an oscillation frequency between 2 Hz and 2 MHz.

83. The apparatus according to claim 79 wherein said predetermined current waveform is periodic and has a magnitude between 10 nA and 1 mA.

84. An apparatus for detection and characterization of one or more medical pathologies within an object under study comprising:
(a) a current source adapted to provide current that electrically stimulates such object;
(b) a plurality of electrodes being disposed relative to such object to receive current from such object, each of said plurality of electrodes being capable of measuring a voltage;
(c) means for controlling such current source and said plurality of electrodes to produce and receive current; and (d) a device coupled to said plurality of electrodes and configured to perform the steps of:
  (i) calculating a plurality of complex impedances, each of said plurality of complex impedances corresponding to a current drive path defined by said current source and one of said plurality of electrodes; and
  (ii) analyzing said plurality of complex impedances to detect and characterize such one or more medical pathologies by solving a continuum electrical model that incorporates nonlinearities.

85. The apparatus according to claim 84 wherein said device is further configured to perform the step of constructing a multidimensional representation of the electrical characteristics of said object under study using said plurality of complex impedances.

86. The apparatus according to claim 85 wherein said device is further configured to perform the step of projecting said multidimensional representation into a plurality of three-dimensional spaces.

87. An apparatus for detection and characterization of one or more medical pathologies within an object under study comprising:
  (a) a current source adapted to provide current that electrically stimulates such object;
  (b) a plurality of electrodes being disposed relative to such object to receive current from such object, each of said plurality of electrodes being capable of measuring a voltage;
  (c) means for controlling such current source and said plurality of electrodes to produce and receive current; and
  (d) a device coupled to said plurality of electrodes and configured to analyze data received from said plurality of electrodes to detect and characterize such one or more medical pathologies by solving a continuum electrical model that incorporates nonlinearities to construct a multidimensional representation of the electrical characteristics of said object under study.

88. The apparatus according to claim 87 wherein said continuum electrical model comprises Zener-diode elements.

89. The apparatus according to claim 87 wherein said continuum electrical model comprises an inductive element.

90. The apparatus according to claim 87 wherein said continuum electrical model comprises:
  (a) an inductive element;
  (b) a capacitive element;
  (c) a resistive element; and
  (d) Zener-diode elements.

91. A method for detection and characterization of one or more medical pathologies within an object under study comprising the steps of:
  (a) stimulating such object electrically with a current source adapted to provide current with a predetermined current waveform;
  (b) measuring a plurality of voltages with a plurality of electrodes disposed relative to such object for receiving current from such object;
  (c) calculating a plurality of complex impedances from said plurality of voltages, each of said plurality of complex impedances corresponding to a current drive path defined by said current source and one of said plurality of electrodes;
  (d) constructing a multidimensional representation of the electrical characteristics of a region within such object using said plurality of complex impedances by solving a continuum electrical model that incorporates nonlinearities; and
  (e) detecting and characterizing such one or more medical pathologies within such object from said multidimensional representation.

92. The method according to claim 91 wherein said current source comprises a plurality of current sources.

93. The method according to claim 91 wherein said plurality of electrodes includes at least one device that is used both as a current source and as a current sink.

94. The method according to claim 91 wherein said plurality of electrodes comprises three electrodes.

95. The method according to claim 91 wherein said plurality of electrodes comprises ten electrodes.

96. The method according to claim 95 wherein said plurality of electrodes are disposed on a pair of gloves, a flexible membrane to attach to skin anywhere, or a ring of electrodes on elastic bands.

97. The method according to claim 91 wherein said plurality of electrodes comprises more than 104 electrodes.

98. The method according to claim 91 wherein said predetermined current waveform is sinusoidal.

99. The method according to claim 91 wherein said predetermined current waveform has a profile selected from the group consisting of square, triangular, ramp, pulse, and sinc.

100. The method according to claim 91 wherein said predetermined current waveform is periodic and comprises an oscillation frequency between 2 Hz and 2 MHz.

101. The method according to claim 91 wherein said predetermined current waveform is periodic and has a magnitude between 10 nA and 1 mA.

102. The method according to claim 91 further comprising the step of reducing electrical noise.

103. The method according to claim 102 wherein said step of reducing electrical noise is accomplished with a lock-in amplifier.

104. The method according to claim 91 further comprising the step of calculating a plurality of complex impedance derivatives with respect to frequency, each of said plurality of complex impedance derivatives corresponding to a current drive path defined by said current source and one of said plurality of electrodes.

105. The method according to claim 91 wherein said continuum electrical model comprises Zener-diode elements.

106. The method according to claim 91 wherein said continuum electrical model comprises an inductive element.

107. The method according to claim 91 wherein said continuum electrical model comprises:
  (a) an inductive element;
  (b) a capacitive element;
  (c) a resistive element; and
  (d) Zener-diode elements.

108. The method according to claim 91 wherein said multidimensional representation is a ten-dimensional representation.

109. The method according to claim 108 wherein said ten-dimensional representation comprises dimensions corresponding to differential cell-membrane capacitance, intracellular-fluid differential resistance, extracellular differential resistance, differential surface membrane inductance, range in variation of said differential cell-membrane capacitance, range in variation of said intracellular-fluid differential resistance, range in variation of said extracellular differential resistance, range in variation of said differential surface membrane inductance, amplitude of said current source, and frequency of said current waveform.

110. The method according to claim 91 wherein said multidimensional representation is a six-dimensional representation.

111. The method according to claim 110 wherein said six-dimensional representation comprises dimensions corresponding to differential cell-membrane capacitance contracted with a range in variation of said differential cell-membrane capacitance, intracellular-fluid differential resistance contracted with a range in variation of said intracellular-fluid differential resistance, extracellular differential resistance contracted with a range in variation of said extracellular differential resistance, differential surface membrane inductance contracted with a range in variation of said differential surface membrane inductance, amplitude of said current source, and frequency of said current waveform.

112. The method according to claim 91 further comprising the step of projecting said multidimensional representation into a plurality of three-dimensional spaces.

113. The method according to claim 112 further comprising the steps of selecting one of said plurality of three-dimensional spaces and displaying the selected three-dimensional space.

114. The method according to claim 91 wherein said step of detecting and characterizing is performed by a trained evaluation system.

115. The method according to claim 114 wherein said trained evaluation system comprises an expert system.

116. The method according to claim 114 wherein said trained evaluation system comprises a neural net.

117. The method according to claim 114 wherein said trained evaluation system uses stochastic optimization.

118. The method according to claim 114 wherein said trained evaluation system uses a genetic algorithm.

119. The method according to claim 91 wherein said object under study comprises a plurality of animal or human tissues.

120. The method according to claim 119 wherein said plurality of animal or human tissues comprises a human breast.

121. The method according to claim 119 wherein said plurality of animal or human tissues comprises a human prostate.

122. The method according to claim 119 wherein said plurality of animal or human tissues comprises a human kidney.

123. The method according to claim 121 wherein said current source is positioned over the lower anterior abdomen of a patient and said plurality of electrodes are disposed on a probe inserted within the rectal cavity of said patient.

124. The method according to claim 119 wherein said plurality of animal or human tissues comprises a human lung.

125. The method according to claim 119 wherein said plurality of animal or human tissues comprises a section of a human alimentary canal.

126. The method according to claim 119 wherein said plurality of animal or human tissues comprises a human liver.

127. The method according to claim 119 wherein said plurality of animal or human tissues comprises lymphatic tissue.

128. The method according to claim 91 wherein said object under study is a surgical specimen.

129. The method according to claim 91 wherein said object under study is a laboratory animal.

130. The method according to claim 91 wherein said object under study is a tissue equivalent model simulator.

131. The method according to claim 91 further comprising the step of generating a compression wave within said object under study.

132. The method according to claim 131 wherein said step of generating is accomplished with an ultrasound source.

133. The method according to claim 131 wherein said step of generating is accomplished by palpation.

134. The method according to claim 91 wherein at least one of said plurality of electrodes is disposed on a glove.

135. The method according to claim 134 further comprising the step of determining the position of said at least one of said plurality of electrodes with respect to said object under study.

136. The method according to claim 135 wherein said step of determining is accomplished with a plurality of position sensors disposed on said glove.

137. The method according to claim 91 further comprising the steps of:
   (a) irradiating, using a radiation source disposed so as to be capable of irradiating such object, upon a volume within the object under study with radiation within a predetermined frequency range or at a predetermined frequency;
   (b) receiving, using a plurality of radiation detectors being disposed relative to such object, radiation scattered by said volume within the object and providing data corresponding to the radiation received; and
   (c) using said data in combination with said plurality of complex impedances to further characterize said one or more medical pathologies within said volume under study.

138. The method according to claim 137 wherein said radiation source is an ultrasound source and said plurality of radiation detectors is a plurality of ultrasound detectors.

139. The method according to claim 138 wherein said ultrasound source and said plurality of ultrasound detectors includes at least one device that is used both as an ultrasound source and as an ultrasound detector.

140. The method according to claim 138 further comprising the step of digitizing said data.

141. The method according to claim 140 wherein said data are digitized at a rate greater than or equal to 30 kHz.

142. The method according to claim 138 wherein said ultrasound source emits monochromatic radiation and said plurality of ultrasound detectors detect only scattered radiation that is at a constant predetermined phase relationship with said monochromatic radiation.

143. The method according to claim 138 wherein said ultrasound source emits monochromatic radiation and said ultrasound detector detects only scattered radiation that is detuned from said monochromatic radiation.

144. The method according to claim 138 wherein said ultrasound source emits chirped radiation.

145. The method according to claim 138 wherein said one or more medical pathologies comprises a cardiac pathology.

146. The method according to claim 145 wherein said cardiac pathology is a valvular dysfunction.

147. The method according to claim 138 wherein said one or more medical pathologies comprises a vascular pathology.

148. The method according to claim 147 further comprising the step of imposing a concentrated magnetic field within said object under study.

149. The method according to claim 148 further comprising the step of scanning said concentrated magnetic field across said object under study.

150. The method according to claim 138 wherein said one or more medical pathologies comprises a pulmonary pathology.

151. The method according to claim 150 wherein said pulmonary pathology is selected from the group consisting of a bronchus spasm, Stein Ron Chi, consolidation, and a neoplasm.

152. The method according to claim 138 wherein said one or more medical pathologies comprises a neurological pathology.

153. The method according to claim 138 wherein said one or more medical pathologies comprises a neuromuscular pathology.

154. The method according to claim 138 wherein said one or more medical pathologies comprises a bone fracture.

155. The method according to claim 91 further comprising the step of analyzing such object with at least one supplementary technique.

156. The method according to claim 155 wherein said step of analyzing is performed prior to said step of measuring to identify a suspicious volume within such object and wherein said region is limited to such suspicious volume.

157. The method according to claim 155 wherein said step of analyzing is performed subsequent to said step of detecting and characterizing.

158. The method according to claim 155 wherein said at least one supplementary technique is a technique selected from the group consisting of x-ray imaging, mammography, computed tomography, magnetic resonance imaging, ultrasound, nuclear medicine, single-photon emission computed tomography, and positron-emission tomography.

159. A method for detection and characterization of one or more medical pathologies within an object under study comprising:
(a) stimulating such object electrically with a current source adapted to provide current with a predetermined current waveform;
(b) measuring a plurality of voltages with a plurality of electrodes disposed relative to such object for receiving current from such object; and
(c) analyzing data received from said plurality of electrodes to detect and characterize such one or more medical pathologies, wherein said analyzing constructs a multidimensional representation of the electrical characteristics of a region within such object by solving a continuum electrical model that incorporates nonlinearities.

160. The method according to claim 159 wherein said predetermined current waveform is sinusoidal.

161. The method according to claim 159 wherein said predetermined current waveform has a profile selected from the group consisting of square, triangular, ramp, pulse, and sinc.

162. The method according to claim 159 wherein said predetermined current waveform is periodic and comprises an oscillation frequency between 2 Hz and 2 MHz.

163. The method according to claim 159 wherein said predetermined current waveform is periodic and has a magnitude between 10 nA and 1 mA.

164. A method for detection and characterization of one or more medical pathologies within an object under study comprising the steps of:
(a) stimulating such object electrically with a current source;
(b) measuring a plurality of voltages with a plurality of electrodes disposed relative to such object for receiving current from such object;
(c) calculating a plurality of complex impedances, each of said plurality of complex impedances corresponding to a current drive path defined by said current source and one of said plurality of electrodes; and
(d) analyzing said plurality of complex impedances to detect and characterize such one or more medical pathologies, wherein said analyzing constructs a multidimensional representation of the electrical characteristics of a region within such object by solving a continuum electrical model that incorporates nonlinearities.

165. The method according to claim 164 further comprising the step of constructing a multidimensional representation of the electrical characteristics of said object under study using said plurality of complex impedances.

166. The method according to claim 165 further comprising the step of projecting said multidimensional representation into a plurality of three-dimensional spaces.

167. A method for detection and characterization of one or more medical pathologies within an object under study comprising:
(a) stimulating such object electrically with a current source;
(b) measuring a plurality of voltages with a plurality of electrodes disposed relative to such object for receiving current from such object; and
(c) analyzing data received from said plurality of electrodes to detect and characterize such one or more medical pathologies by solving a continuum electrical model that incorporates nonlinearities to construct a multidimensional representation of the electrical characteristics of said object under study.

168. The method according to claim 167 wherein said continuum electrical model comprises Zener-diode elements.

169. The method according to claim 167 wherein said continuum electrical model comprises:
(a) an inductive element;
(b) a capacitive element;
(c) a resistive element; and
(d) Zener-diode elements.

* * * * *

UNITED STATES PATENT AND TRADEMARK OFFICE
CERTIFICATE OF CORRECTION

PATENT NO. : 7,499,745 B2  
APPLICATION NO. : 09/794612  
DATED : March 3, 2009  
INVENTOR(S) : Peter Littrup et al.

Page 1 of 1

It is certified that error appears in the above-identified patent and that said Letters Patent is hereby corrected as shown below:

Cover Page, (75) Inventors, delete "Tejeras" and insert --Tijeras--

Column 17, line 31, delete "sin c" and insert --sinc--

Column 19, line 11, delete "prior-aft" and insert --prior-art--

Column 19, line 16, delete "farther" and insert --further--

Signed and Sealed this

Twenty-first Day of April, 2009

JOHN DOLL  
*Acting Director of the United States Patent and Trademark Office*